United States Patent

Müller et al.

[11] Patent Number: 6,054,592
[45] Date of Patent: Apr. 25, 2000

[54] 2-((DIHYDRO) PYRAZOL-3'-YLOXYMETHYLENES

[75] Inventors: Bernd Müller, Frankenthal; Hartmann König, Heidelberg; Reinhard Kirstgen, Neustadt; Klaus Oberdorf, Heidelberg; Franz Röhl, Schifferstadt; Norbert Götz, Worms; Hubert Sauter, Mannheim; Gisela Lorenz, Hambach; Eberhard Ammermann, Heppenheim, all of Germany

[73] Assignee: BASF Aktiengesellschaft, Ludwigshafen, Germany

[21] Appl. No.: 09/131,640

[22] Filed: Aug. 10, 1998

Related U.S. Application Data

[62] Division of application No. 08/765,185, filed as application No. PCT/EP95/02396, Jun. 21, 1995, Pat. No. 5,869,517.

[30] Foreign Application Priority Data

Jul. 6, 1994 [DE] Germany ............... 44 23 612

[51] Int. Cl.[7] ............ C07D 231/22; C07D 403/04
[52] U.S. Cl. ............ 548/371.1; 544/405; 548/366.1; 546/276.1
[58] Field of Search ............ 548/366.1, 371.1; 544/405

[56] References Cited

PUBLICATIONS

Igai et al, *Chemical Abstracts*, vol. 105, No. 2236 1986.

*Primary Examiner*—Robert W. Ramsuer
*Attorney, Agent, or Firm*—Keil & Weinkauf

[57] ABSTRACT

2-[(Dihydro)pyrazol-3'-yloxymethylene]anilides of the formula I

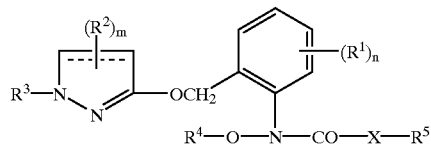

processes and intermediates for their preparation and their use as pesticides and fungicides.

2 Claims, No Drawings

2-((DIHYDRO) PYRAZOL-3'-YLOXYMETHYLENES

This is a divisional of application Ser. No. 08/765,185, filed on Jan. 6, 1997, now U.S. Pat. No. 5,869,517 which is a 371 of PCT/EP95/02396 filed Jun. 21, 1995.

The present invention relates to 2-[(dihydro)pyrazol-3'-yloxy methylene]anilides of the formula I

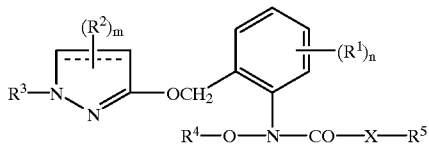

where ... is a single or double bond and the indices and the substituents have the following meanings:

n is 0, 1, 2, 3 or 4, it being possible for the substituents $R^1$ to be different if n is greater than 1;

m is 0, 1 or 2, it being possible for the substituents $R^2$ to be different if m is greater than 1;

X is a direct bond, O or $NR^a$;

$R^a$ is hydrogen, alkyl, alkenyl, alkynyl, cycloalkyl or cycloalkenyl;

$R^1$ is nitro, cyano, halogen,
unsubstituted or substituted alkyl, alkenyl, alkynyl, alkoxy, alkenyloxy, alkynyloxy or
in the case where n is 2, additionally is an unsubstituted or substituted bridge bonded to two adjacent ring atoms and containing three to four members from the group consisting of 3 or 4 carbon atoms, 1 to 3 carbon atoms and 1 or 2 nitrogen, oxygen and/or sulfur atoms, this bridge together with the ring to which it is bonded being able to form a partly unsaturated or aromatic radical;

$R^2$ is nitro, cyano, halogen, $C_1$–$C_4$-alkyl, $C_1$–$C_4$-haloalkyl, $C_1$–$C_4$-alkoxy, $C_1$–$C_4$-alkylthio or $C_1$–$C_4$-alkoxycarbonyl;

$R^3$ is unsubstituted or substituted alkyl, alkenyl or alkynyl;
an unsubstituted or substituted, saturated or mono- or diunsaturated ring which, in addition to carbon atoms, can contain one to three of the following heteroatoms as ring members: oxygen, sulfur and nitrogen, or
an unsubstituted or substituted, mono- or binuclear aromatic radical which, in addition to carbon atoms, can contain one to four nitrogen atoms or one or two nitrogen atoms and one oxygen or sulfur atom or one oxygen or sulfur atom as ring members;

$R^4$ is hydrogen, unsubstituted or substituted alkyl, alkenyl, alkynyl, cycloalkyl, cycloalkenyl, alkylcarbonyl or alkoxycarbonyl;

$R^5$ is alkyl, alkenyl, alkynyl, cycloalkyl or cycloalkenyl, or in the case where X is $NR^a$, additionally is hydrogen.

The invention additionally relates to processes and intermediates for preparing these compounds, compositions containing them and their use for controlling animal pests or harmful fungi.

WO-A 93/15,046 discloses 2-[pyrazolyl-4-oxymethylene]anilides for controlling animal pests and harmful fungi.

The object of the present invention are compounds having an improved action.

We have found that this object is achieved by the compounds defined at the outset. In addition, we have found processes and intermediates for their preparation, mixtures containing them and methods of controlling animal pests and harmful fungi using the compounds I.

The compounds I are obtainable in various ways.

Those compounds I where $R^4$ is hydrogen and X is a direct bond or oxygen are obtained, for example, by converting a benzyl derivative of the formula II in the presence of a base using a 3-hydroxy(dihydro)pyrazole of the formula III to the corresponding 2-[(dihydro)pyrazol-3-yloxymethylene]nitrobenzene of the formula IV, then reducing IV to the N-hydroxyaniline of the formula Va and converting Va to I using a carbonyl compound of the formula VI.

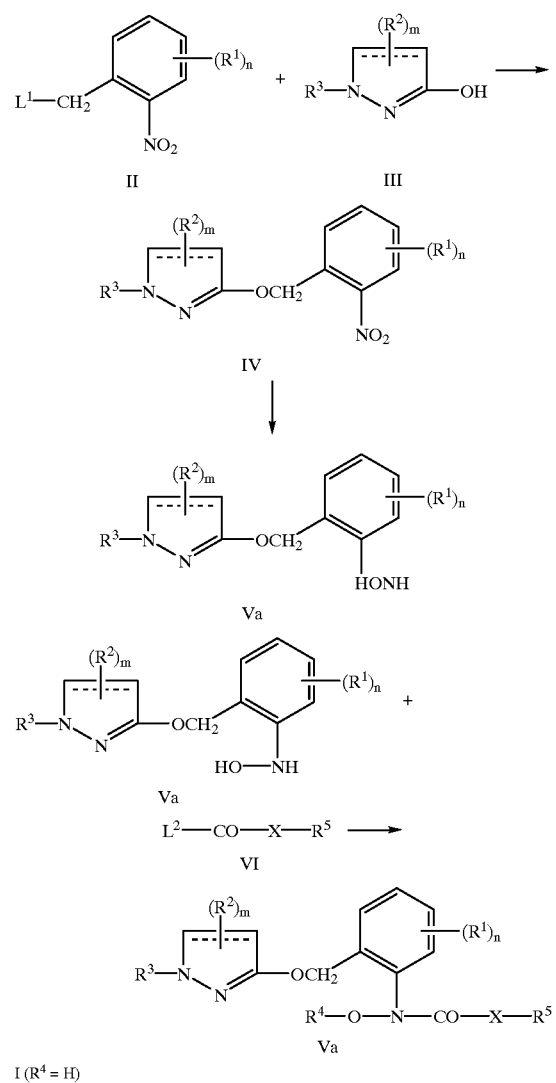

$L^1$ in the formula II and $L^2$ in the formula VI are in each case a nucleophilically replaceable group, for example halogen (eg. chlorine, bromine or iodine) or an alkyl- or arylsulfonate (eg. methylsulfonate, trifluoromethylsulfonate, phenylsulfonate or 4-methylphenylsulfonate).

The etherification of the compounds II and III is customarily carried out at from 0° C. to 80° C., preferably from 20° C. to 60° C.

Suitable solvents are aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, alcohols such as methanol, ethanol, n-propanol, i-propanol, n-butanol and tert-butanol, ketones such as acetone and methyl ethyl ketone, and dimethyl sulfoxide, dimethylformamide, dimethylacetamide, 1,3-dimethylimidazolidin-2-one and 1,2-dimethyltetrahydro-2(1H)-pyrimidine, preferably methylene chloride, acetone, toluene, tert-butyl methyl ether and dimethylformamide. Mixtures of the solvents mentioned can also be used.

Suitable bases are generally inorganic compounds such as alkali metal and alkaline earth metal hydroxides (eg. lithium hydroxide, sodium hydroxide, potassium hydroxide and calcium hydroxide), alkali metal and alkaline earth metal oxides (eg. lithium oxide, sodium oxide, calcium oxide and magnesium oxide), alkali metal and alkaline earth metal hydrides (eg. lithium hydride, sodium hydride, potassium hydride and calcium hydride), alkali metal amides (eg. lithium amide, sodium amide and potassium amide), alkali metal and alkaline earth metal carbonates (eg. lithium carbonate and calcium carbonate) and also alkali metal hydrogen carbonates (eg. sodium hydrogen carbonate), organometallic compounds, in particular alkali metal alkyls (eg. such as methyllithium, butyllithium and phenyllithium), alkylmagnesium halides (eg. methylmagnesium chloride) and also alkali metal and alkaline earth metal alkoxides (eg. sodium methoxide, sodium ethoxide, potassium ethoxide, potassium tert-butoxide and dimethoxymagnesium), additionally organic bases, eg. tertiary amines such as trimethylamine, triethylamine, triisopropylethylamine and N-methylpiperidine, pyridine, substituted pyridines such as collidine, lutidine and 4-dimethylaminopyridine, as well as bicyclic amines.

Sodium hydroxide, potassium carbonate and potassium tert-butoxide are particularly preferred.

The bases are in general used in an equimolar amount, in an excess or if appropriate as a solvent.

It may be advantageous for the reaction to add a catalytic amount of a crown ether (eg. 18-crown-6 or 15-crown-5).

The reaction can also be carried out in two-phase systems consisting of a solution of alkali metal or alkaline earth metal hydroxides or carbonates in water and an organic phase (eg. aromatic and/or halogenated hydrocarbons). Suitable phase transfer catalysts in this case are, for example, ammonium halides and tetrafluoroborates (eg. benzyltriethylammonium chloride, benzyltributylammonium bromide, tetrabutylammonium chloride, hexadecyltrimethylammonium bromide or tetrabutylammonium tetrafluoroborate) and phosphonium halides (eg. tetrabutylphosphonium chloride and tetraphenylphosphonium bromide).

It may be advantageous for the reaction first to convert the 3-hydroxy(dihydro)pyrazole to the corresponding hydroxylate using the base and then to react it with the benzyl derivative.

The starting substances II required for preparing the compounds I are disclosed in EP-A 513 580 or can be prepared by the methods described there [Synthesis 1991, 181; Anal. Chim. Acta 185 (1986), 295; EP-A 336 567].

3-Hydroxypyrazoles IIIa and 3-hydroxydihydropyrazoles IIIb are likewise disclosed in the literature or can be prepared by the methods described there [IIIa: J. Heterocycl. Chem. 30 (1993), 49, Chem. Ber. 107 (1974), 1318, Chem. Pharm. Bull. 19 (1971), 1389, Tetrahedron Lett. 11 (1970), 875, Chem. Herterocycl. Comp. 5 (1969), 527, Chem. Ber. 102 (1969), 3260, Chem. Ber. 109 (1976), 261, J. Org. Chem. 31 (1966), 1538, Tetrahedron Lett. 43 (1987), 607; IIIb: J. Med. Chem. 19 (1976), 715].

The 3-hydroxypyrazoles IIIa are obtained particularly advantageously by the process described in the earlier German Appl.

The nitro compounds IV are reduced to the corresponding N-hydroxyanilines Va in a similar manner to methods known from the literature, for example using metals such as zinc [cf. Ann. Chem. 316 (1901), 278] or with hydrogen (cf. EP-A 085 890).

The N-hydroxyanilines Va are reacted with the carbonyl compounds VI under alkaline conditions, according to the conditions described above for the reaction of the compounds II with the 3-hydroxy(dihydro)pyrazoles III. The reaction is in particular carried out at from −10° C. to 30° C. The preferred solvents are methylene chloride, toluene, tert-butyl methyl ether or ethyl acetate. The preferred bases are sodium hydrogen carbonate, potassium carbonate or aqueous sodium hydroxide solution.

The compounds of the formula I where X is a direct bond or oxygen are additionally obtained, for example, by first reducing a benzyl derivative of the formula IIa to the corresponding hydroxyaniline of the formula Vb, converting Vb using a carbonyl compound of the formula VI to the corresponding anilide of the formula VII, then converting VII using a compound VIII to the amide of the formula IX, then converting IX to the corresponding benzyl halide X and converting X to I in the presence of a base using a 3-hydroxy (dihydro)pyrazole of the formula III.

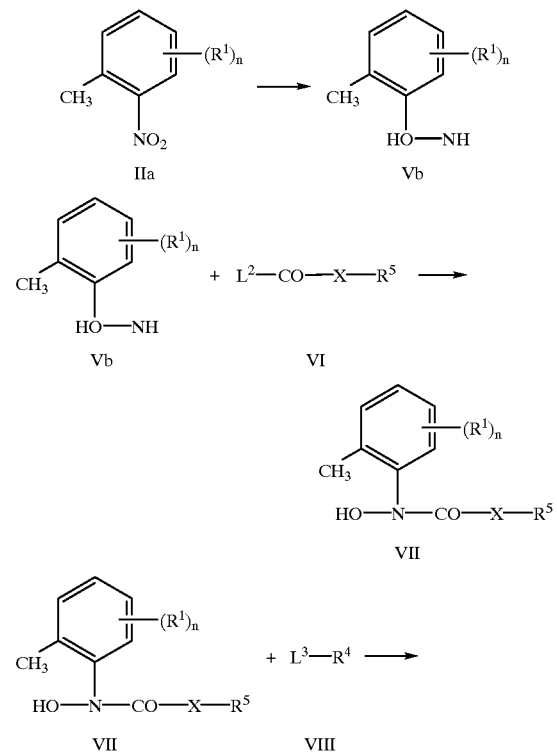

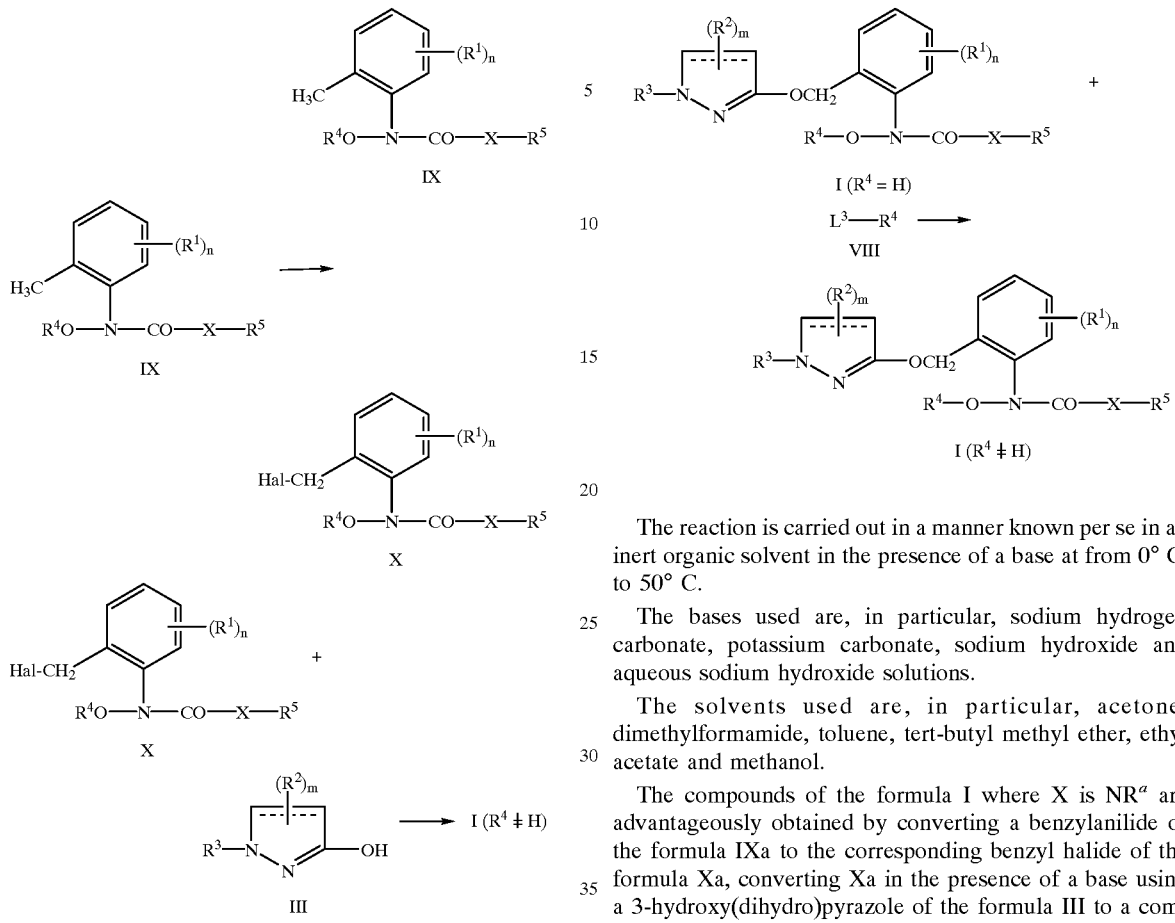

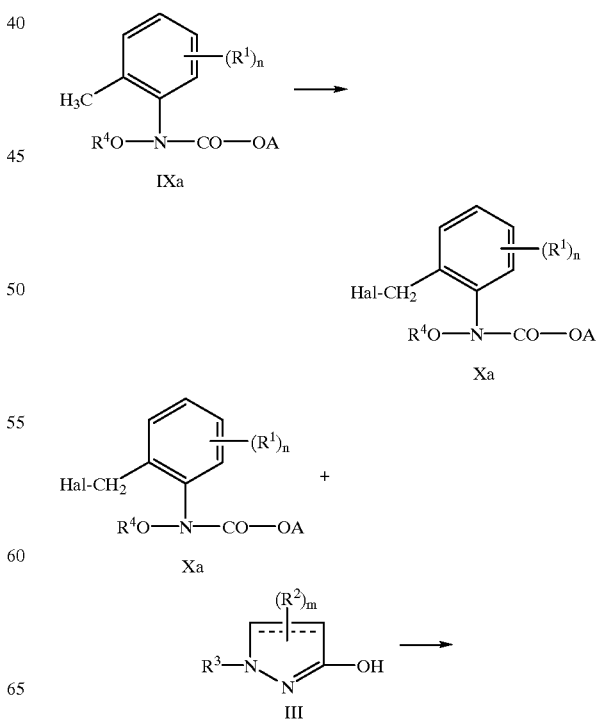

In the formula X, Hal is a halogen atom, in particular chlorine or bromine.

L³ in the formula VIII is a nucleophilically replaceable group, for example halogen (eg. chlorine, bromine or iodine), or an alkyl- or arylsulfonate (eg. methylsulfonate, trifluoromethylsulfonate, phenylsulfonate or 4-methylphenylsulfonate) and $R^4$ is not hydrogen.

The reactions are carried out in a similar manner to the processes mentioned above.

The compounds IX are halogenated using free radicals, it being possible to employ as halogenating agents, for example, N-chloro- or N-bromosuccinimide, elemental halogens (eg. chlorine or bromine) or thionyl chloride, sulfuryl chloride, phosphorus trichloride or phosphorus pentachloride and similar compounds. A radical initiator is customarily additionally used (eg. azobisisobutyronitrile) or the reaction is carried out with irradiation (by UV light). The halogenation is carried out in a manner known per se in a customary organic diluent.

The compounds I where $R^4$ is not hydrogen are additionally obtained by reacting a corresponding compound of the formula I where $R^4$ is hydrogen with a compound of the formula VIII.

The reaction is carried out in a manner known per se in an inert organic solvent in the presence of a base at from 0° C. to 50° C.

The bases used are, in particular, sodium hydrogen carbonate, potassium carbonate, sodium hydroxide and aqueous sodium hydroxide solutions.

The solvents used are, in particular, acetone, dimethylformamide, toluene, tert-butyl methyl ether, ethyl acetate and methanol.

The compounds of the formula I where X is $NR^a$ are advantageously obtained by converting a benzylanilide of the formula IXa to the corresponding benzyl halide of the formula Xa, converting Xa in the presence of a base using a 3-hydroxy(dihydro)pyrazole of the formula III to a compound of the formula I.A and then reacting I.A with a primary or secondary amine of the formula XI to give I.

-continued

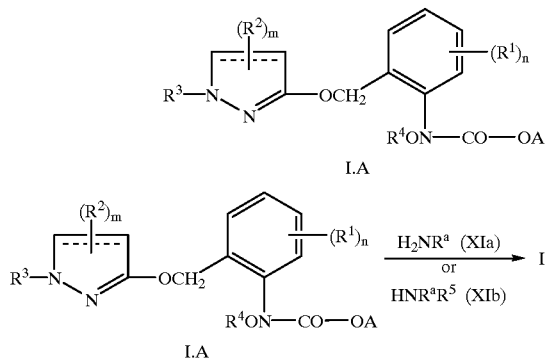

I.A

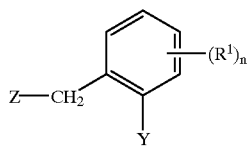 $\xrightarrow[\text{or}]{H_2NR^a \; (XIa)}$ I
HNR$^a$R$^5$ (XIb)

I.A

A in the formula VIIa is alkyl (in particular $C_{1-C_6}$-alkyl) or phenyl; Hal in the formula VIIIa is halogen (in particular chlorine or bromine).

The reactions of IXa to Xa and of Xa to I.A are carried out in general and in particular under the conditions described above.

The compounds I.A are reacted with the primary or secondary amines of the formula XIa or XIb at from 0° C. to 100° C. in an inert solvent or in a solvent mixture.

Suitable solvents are, in particular, water, tert-butyl methyl ether and toluene, or their mixtures. To improve the solubility of the starting materials, it may be advantageous additionally to add one of the following solvents (as solubilizers): tetrahydrofuran, methanol, dimethylformamide and ethylene glycol ether.

The amines XIa and XIb are customarily employed in an excess of up to 100% based on the compounds X or can be used as solvents. With respect to the yield, it may be advantageous to carry out the reaction under pressure.

The compounds I are prepared via intermediates of the formula XII

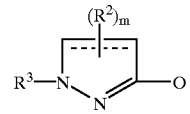

XII where the substituents and the index have the following meanings:

n is 0, 1, 2, 3 or 4, it being possible for the substituents $R^1$ to be different if n is greater than 1;

$R^1$ is nitro, cyano, halogen, unsubstituted or substituted alkyl, alkenyl, alkynyl, alkoxy, alkenyloxy, alkynyloxy or in the case where n is 2, additionally is an unsubstituted or substituted bridge bonded to two adjacent ring atoms and containing three to four members from the group consisting of 3 or 4 carbon atoms, 1 to 3 carbon atoms and 1 or 2 nitrogen, oxygen and/or sulfur atoms, this bridge together with the ring to which it is bonded being able to form a partly unsaturated or aromatic radical;

Y is $NO_2$, NHOH or NHOR$^4$, $R^4$ is unsubstituted or substituted alkyl, alkenyl, alkynyl, cycloalkyl, cycloalkenyl, alkylcarbonyl or alkoxycarbonyl;

Z is hydrogen, hydroxyl, mercapto, cyano, nitro, halogen, $C_1$–$C_6$-alkylsulfonyl, unsubstituted or substituted arylsulfonyl or a group $Z^a$

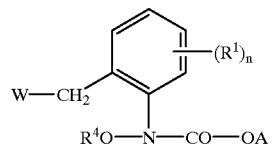

m is 0, 1 or 2, it being possible for the substituents $R^2$ to be different if m is greater than 1;

$R^2$ is nitro, cyano, halogen, $C_1$–$C_4$-alkyl, $C_1$–$C_4$-haloalkyl, $C_1$–$C_4$-alkoxy, $C_1$–$C_4$-alkylthio or $C_1$–$C_4$-alkoxycarbonyl;

$R^3$ is unsubstituted or substituted alkyl, alkenyl or alkynyl;

an unsubstituted or substituted, saturated or mono- or diunsaturated ring which, in addition to carbon atoms, can contain one to three of the following heteroatoms as ring members: oxygen, sulfur and nitrogen, or an unsubstituted or substituted, mono- or binuclear aromatic radical which, in addition to carbon atoms, can contain one to four nitrogen atoms or one or two nitrogen atoms and one oxygen or sulfur atom or one oxygen or sulfur atom as ring members.

In particular, intermediates of the formula XII are preferred in the preparation where Y is NHOH and Z is the group $Z^a$.

Additionally, intermediates of the formula IX are preferred in the preparation where Y is $NO_2$ and Z is the group $Z^a$.

With respect to the preparation of the compounds I where X, is NR$^a$, intermediates of the general formula XIII

XIII are preferred where the substituents $R^1$ and $R^4$ and also the index n have the meanings given at the outset and the substituents W and A have the following meanings:

W is hydrogen, halogen or $Z^a$, and

A is alkyl or phenyl.

In particular, compounds XIII are preferred in this case where the substituent W is hydrogen, chlorine, bromine or $Z^a$.

Additionally, those compounds XIII are preferred where the substituent A is $C_1$–$C_6$-alkyl.

In particular, those compounds XIII are also particularly preferred where the substituent A is phenyl.

Equally preferred are those compounds XIII where $R^4$ is hydrogen, ethyl or ethyl.

In addition, compounds XIII are preferred where n is 0 or 1.

Particularly preferred compounds XIII are those where the substituents and the index have the following meanings:

is 0,

W is hydrogen, chlorine, bromine or $Z^a$, $R^4$ is hydrogen, methyl or ethyl and A is phenyl.

The compounds I can contain acidic or basic centers and accordingly form acid addition products or base addition products or salts.

Acids for acid addition products are, inter alia, inorganic acids (eg. hydrohalic acids such as hydrochloric and hydrobromic acid, phosphoric acid, sulfuric acid, nitric acid), organic acids (eg. formic acid, acetic acid, oxalic acid, malonic acid, lactic acid, malic acid, succinic acid, tartaric acid, citric acid, salicylic acid, p-toluenesulfonic acid, dodecylbenzenesulfonic acid) or other proton acid compounds (eg. saccharin). Bases for base addition products are, inter alia, oxides, hydroxides, carbonates or hydrogen carbonates of alkali metals or alkaline earth metals (eg. potassium or sodium hydroxide or carbonate) or ammonium compounds (eg. ammonium hydroxide).

In the definitions of the symbols given in the above formulae collective terms were in some cases used which are generally representative of the following substituents:

halogen: fluorine, chlorine, bromine and iodine;

alkyl: saturated, straight-chain or branched hydrocarbon radicals having 1 to 4 or 10 carbon atoms, eg. methyl, ethyl, propyl, 1-methylethyl, butyl, 1-methylpropyl, 2-methylpropyl and 1,1-dimethylethyl;

haloalkyl: straight-chain or branched alkyl groups having 1 to 4 carbon atoms (as mentioned above), it being possible for the hydrogen atoms in these groups to be partly or completely replaced by halogen atoms as mentioned above, eg. $C_1$–$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkylcarbonyl: straight-chain or branched alkyl groups, in particular having 1 to 10 carbon atoms (as mentioned above), which are bonded to the structure via a carbonyl group (—CO—);

alkoxy: straight-chain or branched alkyl groups having 1 to 4 or 10 carbon atoms (as mentioned above), which are bonded to the structure via an oxygen atom (—O—);

alkoxycarbonyl: straight-chain or branched alkoxy groups having 1 to 4 carbon atoms (as mentioned above), which are bonded to the structure via a carbonyl group (—C—);

alkylthio: straight-chain or branched alkyl groups having 1 to 4 carbon atoms (as mentioned above), which are bonded to the structure via a sulfur atom (—S—);

unsubstituted or substituted alkyl: saturated, straight-chain or branched hydrocarbon radicals, in particular having 1 to 10 carbon atoms, eg. $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methyl-propyl and 1-ethyl-2-methylpropyl;

unsubstituted or substituted alkenyl: unsaturated, straight-chain or branched hydrocarbon radicals, in particular having 2 to 10 carbon atoms and a double bond in any desired position, eg. $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1ethyl-1-methyl-2-propenyl, 1-ethyl-2-methyl-1-propenyl and 1-ethyl-2-methyl-2-propenyl;

unsubstituted or substituted alkenyloxy: straight-chain or branched alkenyl groups having 3 to 10 carbon atoms (as mentioned above), which are bonded to the structure via an oxygen atom alkynyl: straight-chain or branched hydrocarbon groups, in particular having 2 to 20 carbon atoms and a triple bond in any desired position, eg. $C_2$–$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl,2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

unsubstituted or substituted alkynyloxy: straight-chain or branched alkynyl groups having 3 to 10 carbon atoms (as mentioned above), which are bonded to the structure via an oxygen atom (—O—);

unsubstituted or substituted cycloalkyl: mono- or bicyclic hydrocarbon radicals having 3 to 10 carbon atoms, eg. $C_3$–$C_{10}$-(bi)cycloalkyl such as cyclopropyl, cyclobutyl, cyclopentyl, cyclohexyl, cycloheptyl, bornanyl, norbornanyl, dicyclohexyl, bicyclo[3.3.0]octyl, bicyclo[3.2.1]octyl, bicyclo[2.2.2]octyl or bicyclo[3.3.1]nonyl;

unsubstituted or substituted cycloalkenyl: mono- or bicyclic hydrocarbon radicals having 5 to 10 carbon atoms and a double bond in any desired ring position, eg. $C_5$–$C_{10}$-(bi)cycloalkenyl such as cyclopentenyl, cyclohexenyl, cycloheptenyl, bornenyl, norbornenyl, dicyclohexenyl and bicyclo[3.3.0]octenyl; an unsubstituted or substituted bridge bonded to two adjacent ring atoms, which contains three to four members from the group consisting of 3 or 4 carbon atoms, 1 to 3 carbon atoms and 1 or 2 nitrogen, oxygen and/or sulfur atoms, this bridge together with the ring to which it is bonded being able to form a partly unsaturated or aromatic radical: bridges which, with the ring to which they are bonded, form, for example, one of the following systems: quinolinyl, benzofuranyl or naphthyl;

an unsubstituted or substituted, saturated or mono- or diunsaturated ring which, in addition to carbon atoms, can contain one to three of the following heteroatoms as ring members: oxygen, sulfur and nitrogen, for example carbocycles such as cyclopropyl, cyclopentyl, cyclohexyl, cyclopent-2-enyl, cyclo-hex-2-enyl, 5- to 6-membered, saturated or unsaturated heterocycles, containing one to three nitrogen atoms and/or one oxygen or sulfur atom such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl,1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-tetrahydropyridazinyl, 4-tetrahydropyridazinyl, 2-tetrahydropyrimidinyl, 4-tetrahydropyrimidinyl, 5-tetrahydropyrimidin2-tetra2-tetrahydropyrazinyl, 1,3,5-tetrahydro-triazin-2-yl and 1,2,4-tetrahydrotriazin-3-yl preferably 2-tetrahydrofuranyl, 2-tetrahydrothienyl, 2-pyrrolidinyl, 3-isoxazolidinyl, 3-isothiazolidinyl, 1,3,4-oxazolidin-2-yl, 2,3-dihydrothien-2-yl, 4,5-isoxazolin-3-yl, 3-piperidinyl, 1,3dioxan-5-yl, 4-piperidinyl, 2-tetrahydropyranyl, 4-tetrahydropyranyl;

or an unsubstituted or substituted, mono- or binuclear aromatic ring system which, in addition to carbon atoms, can contain one to four nitrogen atoms or one or two nitrogen atoms and one oxygen or sulfur atom or one oxygen or sulfur atom as ring members, ie. aryl radicals such as phenyl and naphthyl, preferably phenyl or 1- or 2-naphthyl, and hetaryl radicals, for example 5-membered ring heteroaromatics containing one to three nitrogen atoms and/or one oxygen or sulfur atom such as 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,5-triazol-3-yl, 1,2,3-triazol-4-yl, 1,2,3-triazol-5-yl, 1,2,3-triazol-4-yl, 5-tetrazolyl, 1,2,3,4-thiatriazol-5-yl and 1,2,3,4-oxatriazol-5-yl, in particular 3-isoxazolyl, 5-isoxazolyl, 4-oxazolyl, 4-thiazolyl, 1,3,4-oxadiazol-2-yl and 1,3,4-thiadiazol-2-yl;

six-membered ring heteroaromatics containing one to four nitrogen atoms as heteroatoms, such as 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl, in particular 2-pyridinyl, 3-pyridinyl, 4-pyridinyl, 2-pyrimidinyl, 4-pyrimidinyl, 2-pyrazinyl and 4-pyridazinyl, The addition of unsubstituted or substituted with respect to alkyl, alkenyl and alkynyl groups is intended to express that these groups can be partly or completely halogenated (ie. the hydrogen atoms of these groups can be partly or completely replaced by identical or different halogen atoms as mentioned above (preferably fluorine, chlorine and bromine, in particular fluorine an d chlorine) and/or can carry one to three, in particular one, of the following radicals:

$C_1$–$C_6$-alkoxy, $C_1$–$C_6$-haloalkoxy, $C_1$–$C_6$-alkylthio, $C_{1-6}$-haloalkylthio, $C_1$–$C_6$-alkylamino, di-$C_1$–$C_6$-alkylamino, $C_2$–$C_6$-alkenyloxy, $C_2$–$C_6$-haloalkenyloxy, $C_2$–$C_6$-alkynyloxy, $C_2$–$C_6$-haloalkynyloxy, $C_3$–$C_6$cycloalkyl, $C_{3-C6}$-cycloalkyloxy, $C_3$–$C_6$-cycloalkenyl, $C_3$–$C_6$-cycloalkenyloxy, or an unsubstituted or substituted, mono- or binuclear aromatic ring system which, in addition to carbon atoms, can contain one to four nitrogen atoms or one or two nitrogen atoms and one oxygen or sulfur atom or one oxygen or sulfur atom as ring members (as mentioned above), which can be bonded to the substituents directly or via an oxygen atom (—O—), a sulfur atom (—S—) or an amino group (—$NR^a$—), ie. aryl radicals such as phenyl and naphthyl, preferably phenyl or 1- or 2-naphthyl, and hetaryl radicals, for example 5-membered ring heteroaromatics containing one to three nitrogen atoms and/or one oxygen or sulfur atom such as 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,2,4-oxadiazol-3-yl, 1,2,4-oxadiazol-5-yl, 1,2,4-thiadiazol-3-yl, 1,2,4- thiadiazol-5-yl, 1,2,5-triazol-3-yl, 1,2,3-triazol-4-yl, 1,2,3-triazol-5-yl, 1,2,3-triazol-4-yl, 5-tetrazolyl, 1,2,3,4-thiatriazol-5-yl and 1,2,3,4-oxatriazol-5-yl, in particular 3-isoxazolyl, 5-isoxazolyl, 4-oxazolyl, 4-thiazolyl, 1,3,4-oxadiazol-2-yl and 1,3,4-thiadiazol-2-yl;

six-membered ring heteroaromatics containing one to four nitrogen atoms as heteroatoms, such as 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl, in particular 2-pyridinyl, 3-pyridinyl, 4-pyridinyl, 2-pyrimidinyl, 4-pyrimidinyl, 2-pyrazinyl and 4-pyridazinyl.

The mono- or binuclear aromatic or heteroaromatic systems mentioned under the radicals can in turn be partly or completely halogenated, ie. the hydrogen atoms of these groups can be partly or completely replaced by halogen atoms such as fluorine, chlorine, bromine and iodine, preferably fluorine and chlorine.

In addition to the halogen atoms designated, these mono- or binuclear aromatic or heteroaromatic systems can carry one to three of the following substituents:

nitro;

cyano, thiocyanato;

alkyl, particularly $C_1$–$C_6$-alkyl as mentioned above, preferably methyl, ethyl, 1-methylethyl, 1,1-dimethylethyl, butyl, hexyl, in particular methyl and 1-methylethyl;

$C_1$–$C_4$-haloalkyl, as mentioned above, preferably trichloromethyl, difluoromethyl, trifluoromethyl, 2,2-difluoroethyl, 2,2,2-trifluoroethyl and pentafluoroethyl;

$C_1$–$C_4$-alkoxy, preferably methoxy, ethoxy, 1-methylethoxy and 1,1-dimethylethoxy, in particular methoxy;

$C_1$–$C_4$-haloalkoxy, particularly $C_1$–$C_2$-haloalkoxy, preferably difluoromethyloxy, trifluoromethyloxy and 2,2,2-trifluoroethyloxy, in particular difluoromethyloxy;

$C_1$–$C_4$-alkylthio, preferably methylthio and 1-methylethylthio, in particular methylthio;

$C_1$–$C_4$-alkylamino such as methylamino, ethylamino, propylamino, 1-methylethylamino, butylamino, 1-methylpropylamino, 2-methylpropylamino and 1,1-dimethylethylamino, preferably methylamino and 1,1-dimethylethylamino, in particular methylamino, di-$C_1$–$C_4$-alkylamino such as N,N-dimethylamino, N,N-diethylamino, N,N-dipropylamino, N,N-di-(1-methylethyl)amino, N,N-dibutylamino, N,N-di-(1-methylpropyl)amino, N,N-di-(2-methylpropyl)amino, N,N-di-(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl) amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl) amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl) amino, N-butyl-N-(1,1-dimethylethyl)amino, N-(1-methylpropyl)-N-(2-methylpropyl)amino, N-(1,1-dimethylethyl)-N-(1-methylpropyl)amino and N-(1,1-dimethylethyl)N-(2 -methylpropyl)amino, preferably N,N-dimethylamino and N,N-diethylamino, in particular N,N-dimethylamino;

$C_1$–$C_6$-alkylcarbonyl such as methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl and 1-ethyl-2-methylpropylcarbonyl, preferably methylcarbonyl, ethylcarbonyl and 1,1-dimethylcarbonyl, in particular ethylcarbonyl;

$C_1$–$C_6$-alkoxycarbonyl such as methoxycarbonyl, ethoxycarbonyl, propyloxycarbonyl, 1-methylethoxycarbonyl, butyloxycarbonyl, 1-methylpropyloxycarbonyl, 2-methylpropyloxycarbonyl, 1,1-dimethylethoxycarbonyl, pentyloxycarbonyl, 1-methylbutyloxycarbonyl, 2-methylbutyloxycarbonyl, 3-methylbutyloxycarbonyl, 2,2-dimethylpropyloxycarbonyl, 1-ethylpropyloxycarbonyl, hexyloxycarbonyl, 1,1-dimethylpropoxycarbonyl, 1,2-dimethylpropyloxycarbonyl, 1-methylpentyloxycarbonyl, 2-methylpentyloxycarbonyl, 3-methylpentyloxycarbonyl, 4-methylpentyloxycarbonyl, 1,1-dimethylbutyloxycarbonyl, 1,2-dimethylbutyloxycarbonyl, 1,3-dimethylbutyloxycarbonyl, 2,2-dimethylbutyloxycarbonyl, 2,3-dimethylbutyloxycarbonyl, 3,3-dimethylbutyloxycarbonyl, 1-ethylbutyloxycarbonyl, 2-ethylbutyloxycarbonyl, 1,1,2-trimethylpropyloxycarbonyl, 1,2,2-trimethylpropyloxycarbonyl, 1-ethyl-1-methylpropyloxycarbonyl and 1-ethyl-2-methylpropyloxycarbonyl, preferably methoxycarbonyl, ethoxycarbonyl and 1,1-dimethylethoxycarbonyl, in particular ethoxycarbonyl; $C_1$–$C_6$-alkylaminocarbonyl such as methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl, 1,1-dimethylethylaminocarbonyl, pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylamino carbonyl, 1,2-dimethylbutylaminocarbonyl, 1,3- dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl and 1-ethyl-2-methylpropylaminocarbonyl, preferably methylaminocarbonyl and ethylaminocarbonyl, in particular methylaminocarbonyl;

di-$C_1$–$C_6$-alkylaminocarbonyl, particularly di-$C_1$–$C_4$-alkylaminocarbonyl such as N,N-dimethylaminocarbonyl, N,N-diethylaminocarbonyl, N,N-dipropylaminocarbonyl, N,N-di-(1-methylethyl)aminocarbonyl, N,N-dibutylaminocarbonyl, N,N-di-(1-methylpropyl)aminocarbonyl, N,N-di-(2-methylpropyl)aminocarbonyl, N,N-di-(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(l-methylpropyl)aminocarbonyl, N-ethyl-N-(2-methylpropyl)aminocarbonyl, N-ethyl-N-(1,1-dimethylethyl) aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methyl-propyl)aminocarbonyl, N-(1,1-dimethylethyl)-N-(1-methylpropyl)aminocarbonyl and N-(1,1-dimethylethyl)-N-(2-methylpropyl)aminocarbonyl, preferably N,N-dimethylaminocarbonyl and N,N-diethylaminocarbonyl, in particular N,N-dimethylaminocarbonyl;

$C_1$–$C_6$-alkylcarboxyl such as methylcarboxyl, ethylcarboxyl, propylcarboxyl, 1-methylethylcarboxyl, butylcarboxyl, 1-methylpropylcarboxyl, 2-methylpropylcarboxyl, 1,1-dimethylethylcarboxyl, pentylcarboxyl, 1-methylbutylcarboxyl, 2-methylbutylcarboxyl, 3-methylbutylcarboxyl, 1,1-dimethylpropylcarboxyl, 1,2-dimethylpropylcarboxyl, 2,2-dimethylpropylcarboxyl, 1-ethylpropylcarboxyl, hexylcarboxyl, 1-methylpentylcarboxyl, 2-methylpentylcarboxyl, 3-methylpentylcarboxyl, 4-methylpentylcarboxyl, 1,1-dimethylbutylcarboxyl, 1,2-dimethylbutylcarboxyl, 1,3-dimethylbutylcarboxyl, 2,2-dimethylbutylcarboxyl, 2,3-dimethylbutylcarboxyl, 3,3-dimethylbutylcarboxyl, 1-ethylbutylcarboxyl, 2-ethylbutylcarboxyl, 1,1,2-trimethylpropylcarboxyl, 1,2,2-trimethylpropylcarboxyl, 1-ethyl-1-methylpropylcarboxyl and 1-ethyl-2-methylpropylcarboxyl, preferably methylcarboxyl, ethylcarboxyl and 1,1-dimethylethylcarbonyl, in particular methylcarboxyl and 1,1-dimethylethylcarboxyl; $C_1$–$C_6$-alkylcarbonylamino such as methylcarbonylamino, ethylcarbonylamino, propylcarbonylamino, 1-methylethylcarbonylamino, butylcarbonylamino, 1-methylpropylcarbonylamino, 2-methylpropylcarbonylamino, 1,1-dimethylethylcarbonylamino, pentylcarbonylamino, 1-methylbutylcarbonylamino, 2-methylbutylcarbonylamino, 3-methylbutylcarbonylamino, 2,2-dimethylpropylcarbonylamino, 1-ethylpropylcarbonylamino, hexylcarbonylamino, 1,1-dimethylpropylcarbonylamino, 1,2-dimethylpropylcarbonylamino, 1-methylpentylcarbonylamino, 2-methylpentylcarbonylamino, 3-methylpentylcarbonylamino, 4-methylpentylcarbonylamino, 1,1-dimethylbutylcarbonylamino, 1,2-dimethylbutylcarbonylamino, 1,3-dimethylbutylcarbonylamino, 2,2-dimethylbutylcarbonylamino, 2,3-dimethylbutylcarbonylamino, 3,3-dimethylbutylcarbonylamino, 1-ethylbutylcarbonylamino, 2-ethylbutylcarbonylamino, 1,1,2-trimethylpropylcarbonylamino, 1,2,2-trimethylpropylcarbonylamino, 1-ethyl-1-methylpropylcarbonylamino and 1-ethyl-2-methylpropylcarbonylamino, preferably methylcarbonylamino and ethylcarbonylamino, in particular ethylcarbonylamino;

$C_3$–$C_7$-cycloalkyl such as cyclopropyl, cyclobutyl, cyclopentyl, cyclohexyl and cycloheptyl, preferably cyclopropyl, cyclopentyl and cyclohexyl, in particular cyclopropyl;

$C_3$–$C_7$-cycloalkoxy such as cyclopropyloxy, cyclobutyloxy, cyclopentyloxy, cyclohexyloxy and cycloheptyloxy, preferably cyclopentyloxy and cyclohexyloxy, in particular cyclohexyloxy;

$C_3$–$C_7$-cycloalkylthio such as cyclopropylthio, cyclobutylthio, cyclopentylthio, cyclohexylthio and cycloheptylthio, preferably cyclohexylthio;

$C_3$–$C_7$-cycloalkylamino such as cyclopropylamino, cyclobutylamino, cyclopentylamino, cyclohexylamino and cycloheptylamino, preferably cyclopropylamino and cyclohexylamino, in particular cyclopropylamino.

In addition to the abovementioned substituents, the mono- or binuclear aromatic or heteroaromatic systems can also carry a radical —CR'=NOR", where the radicals R' and R" are the following groups:

R' hydrogen, cyano, alkyl (preferably $C_1$–$C_6$-alkyl, in particular $C_1$–$C_4$-alkyl), haloalkyl (preferably $C_1$–$C_4$-haloalkyl, in particular $C_1$–$C_2$-haloalkyl), alkenyl (preferably $C_2$–$C_6$-alkenyl, in particular $C_2$–$C_4$-alkenyl), haloalkenyl (preferably $C_2$–$C_6$-haloalkenyl, in particular $C_2$–$C_4$-haloalkenyl), alkynyl (preferably $C_2$–$C_6$-alkynyl, in particular $C_2$–$C_4$-alkynyl), haloalkynyl (preferably $C_2$–$C_6$-haloalkynyl, in particular $C_2$–$C_4$-haloalkynyl) and cycloalkyl (preferably $C_3$–$C_8$-cycloalkyl, in particular $C_3$–$C_6$-cycloalkyl);

R" alkyl (preferably $C_1$–$C_6$-alkyl, in particular $C_1$–$C_4$-alkyl), haloalkyl (preferably $C_1$–$C_4$-haloalkyl, in particular $C_1$–$C_2$-haloalkyl), alkenyl (preferably $C_2$–$C_6$- alkenyl, in particular $C_2$–$C_4$-alkenyl), haloalkenyl (preferably $C_2$–$C_6$-haloalkenyl, in particular $C_2$–$C_4$-haloalkenyl), alkynyl (preferably $C_2$–$C_6$-alkynyl, in particular $C_2$–$C_4$-alkynyl), haloalkynyl (preferably $C_2$–$C_6$-haloalkynyl, in particular $C_{2-4}$-haloalkynyl) and cycloalkyl (preferably $C_3$–$C_8$-cycloalkyl, in particular $C_3$–$C_6$-cycloalkyl).

With respect to their biological action, compounds I are preferred where—is a double bond.

In addition, compounds I are preferred where the ═ is a single bond.

Equally, compounds I are preferred where n is 0 or 1, in particular 0.

Additionally, compounds I are preferred where $R^1$ is halogen, $C_1$–$C_4$-alkyl, $C_1$–$C_2$-haloalkyl, $C_1$–$C_4$-alkoxy or $C_1$–$C_2$-haloalkoxy.

In addition, compounds I are preferred where m is 0 or 1.

Equally, compounds I are preferred where $R^2$ is nitro, halogen, $C_1$–$C_4$-alkyl, $C_1$–$C_4$-haloalkyl, $C_1$–$C_4$-alkoxy or $C_1$–$C_4$-alkoxycarbonyl.

In addition, compounds I are preferred where $R^3$ is $C_1$–$C_4$-alkyl or $C_3$–$C_6$-cycloalkyl.

Additionally, compounds I are preferred where $R^3$ is an unsubstituted or substituted, mono- or binuclear aromatic radical which, in addition to carbon atoms, can contain one to four nitrogen atoms or one or two nitrogen atoms and one oxygen or sulfur atom or one oxygen or sulfur atom as ring members.

In particular, compounds I are preferred where $R^3$ is phenyl or benzyl, where the phenyl radical can be partly or completely halogenated and/or can carry one to three of the following radicals: cyano, nitro, $C_1$–$C_6$-alkyl, $C_1$–$C_4$-haloalkyl, $C_1$–$C_4$-alkoxy, $C_1$–$C_4$-haloalkoxy, $C_1$–$C_4$-alkoxy-$C_1$–$C_4$-alkyl, $C_3$–$C_6$-cycloalkyl, $C_1$–$C_4$-alkylcarbonyl, $C_1$–$C_4$-alkoxycarbonyl, phenyl, phenoxy and phenyl-$C_1$–$C_4$-alkoxy, where the phenyl rings in turn can be partly or completely halogenated and/or can carry one to three of the following radicals: cyano, nitro, $C_1$–$C_4$-alkyl, $C_1$–$C_2$-haloalkyl, $C_1$–$C_4$-alkoxy, $C_1$–$C_2$-haloalkoxy, $C_3$–$C_6$-cycloalkyl, $C_1$–$C_4$-alkylcarbonyl or $C_1$–$C_4$-alkoxycarbonyl, and/or a group CR'═NOR", where R' is hydrogen or $C_1$–$C_4$-alkyl and R" is $C_1$–$C_6$-alkyl, and/or two adjacent C atoms of the phenyl ring via an oxy-$C_1$–$C_3$-alkoxy bridge or an oxy-$C_1$–$C_3$-haloalkoxy bridge.

Additionally, compounds I are particularly preferred where $R^3$ is pyridyl or pyrimidyl, it being possible for the pyridyl ring to be partly or completely halogenated and/or to carry one to three of the following radicals: cyano, nitro, $C_1$–$C_4$-alkyl, $C_1$–$C_2$-haloalkyl, $C_1$–$C_4$-alkoxy, $C_1$–$C_2$-haloalkoxy, $C_3$–$C_6$-cycloalkyl, $C_1$–$C_4$-alkylcarbonyl or $C_1$–$C_4$-alkoxycarbonyl.

In addition, compounds I are preferred where $R^4$ is hydrogen, $C_1$–$C_4$-alkyl or $C_1$–$C_2$-haloalkyl.

Additionally, compounds I are preferred where $R^5X$ is methyl, ethyl, methoxy or methylamino.

Examples of particularly preferred compounds I are compiled in the Tables.

Table 1
Compounds of the general formula I.1 where $R^4$ is methyl, $R^5X$ is methyl and $R^x_p$ is a substituent of one line of Table A

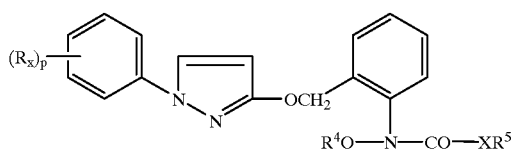

I.1

Table 2
Compounds of the general formula I.1 where $R^4$ is methyl, $R^5X$ is ethyl and $R^x_p$ is a substituent of one line of Table A Table 3
Compounds of the general formula I.2 where $R^4$ is methyl, $R^5X$ is methyl and $R^x_p$ is a substituent of one line of Table A

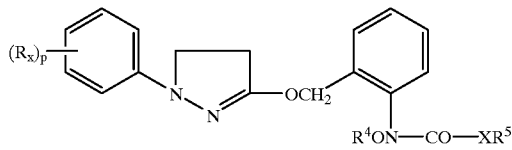

I.2

Table 4
Compounds of the general formula I.2 where $R^4$ is methyl, $R^5X$ is ethyl and $R^x_p$ is a substituent of one line of Table A Table 5
Compounds of the general formula I.1 where $R^4$ is methyl, $R^5X$ is methoxy and $R^x_p$ is a substituent of one line of Table A Table 6
Compounds of the general formula I.2 where $R^4$ is methyl, $R^5X$ is methoxy, $R^2$ is methoxy and $R^x_p$ is a substituent of one line of Table A Table 7
Compounds of the general formula I.1 where $R^4$ is methyl, $R^5X$ is methylamino and $R^x_p$ is a substituent of one line of Table A Table 8
Compounds of the general formula I.2 where $R^4$ is methyl, $R^5X$ is methylamino and $R^x_p$ is a substituent of one line of Table A Table 9
Compounds of the general formula I.3 where $R^4$ is methyl, $R^5X$ is methyl, $R^y$ is hydrogen, $R^z$ is chlorine and $R^x_p$ is a substituent of one line of Table A

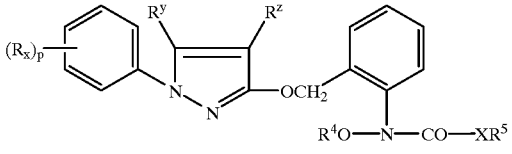

I.3

Table 10
Compounds of the general formula I.3 where $R^4$ is methyl, $R^5X$ is ethyl, $R^y$ is hydrogen, $R^z$ is chlorine and $R^x_p$ is a substituent of one line of Table A Table 11
Compounds of the general formula I.3 where $R^4$ is methyl, $R^5X$ is methoxy, $R_y$ is hydrogen, $R^z$ is chlorine and $R^x_p$ is a substituent of one line of Table A Table 12
Compounds of the general formula I.3 where $R^4$ is methyl, $R^5X$ is methylamino, $R^y$ is hydrogen, $R^z$ is chlorine and $R^x_p$ is a substituent of one line of Table A Table 13
Compounds of the general formula I.3 where $R^4$ is methyl, $R^5X$ is methyl, $R^y$ is methyl, $R^z$ is hydrogen and $R^x_p$ is a substituent of one line of Table A Table 14
Compounds of the general formula I.3 where $R^4$ is methyl, $R^5X$ is ethyl, $R^y$ is methyl, $R^z$ is hydrogen and $R^x_p$ is a substituent of one line of Table A Table 15
Compounds of the general formula I.3 where $R^4$ is methyl, $R^5X$ is methoxy, $R^y$ is methyl, $R^z$ is hydrogen and $R^x_p$ is a substituent of one line of Table A Table 16
Compounds of the general formula I.3 where $R^4$ is methyl, $R^5X$ is methylamino, $R^y$ is methyl, $R^z$ is hydrogen and $R^x_p$ is a substituent of one line of Table A Table 17
Compounds of the general formula I.3 where $R^4$ is methyl, $R^5X$ is methyl, $R^y$ is trifluoromethyl, $R^z$ is hydrogen and $R^x_p$ is a substituent of one line of Table A Table 18
Compounds of the general formula I.3 where $R^4$ is methyl, $R^5X$ is ethyl, $R^y$ is trifluoromethyl, $R^z$ is hydrogen and $R^x_p$ is a substituent of one line of Table A Table 19
Compounds of the general formula I.3 where $R^4$ is methyl, $R^5X$ is methoxy, $R^y$ is trifluoromethyl, $R^z$ is hydrogen and $R^x_p$ is a substituent of one line of Table A Table 20
Compounds of the general formula I.3 where $R^4$ is methyl, $R^5X$ is methylamino, $R^y$ is trifluoromethyl, $R^z$ is hydrogen and $R^x_p$ is a substituent of one line of Table A Table 21
Compounds of the general formula I.4 where $R^5X$ is methyl and the combination of the substituents $R^1$, $R^y$, $R^z$, $R^3$ and $R^4$ is a compound, in each case of one line of Table B

I.4

Table 22
Compounds of the general formula I.4 where $R^5X$ is ethyl and the combination of the substituents $R^1$, $R^y$, $R^z$, $R^3$ and $R^4$ is a compound, in each case of one line of Table B Table 23
Compounds of the general formula I.4 where $R^5X$ is methoxy and the combination of the substituents $R^1$, $R^y$, $R^z$, $R^3$ and $R^4$ is a compound, in each case of one line of Table B Table 24
Compounds of the general formula I.4 where $R^5X$ is methylamino and the combination of the substituents $R^1$, $R^y$, $R^z$, $R^3$ and $R^4$ is a compound, in each case of one line of Table B Table 25
Compounds of the general formula I.1 where $R^4$ is hydrogen, $R^5X$ is methyl and $R^x_p$ is a substituent of one line of Table A Table 26
Compounds of the general formula I.1 where $R^4$ is hydrogen, $R^5X$ is ethyl and $R^x_p$ is a substituent of one line of Table A Table 27
Compounds of the general formula I.2 where $R^4$ is hydrogen, $R^5X$ is methyl and $R^x_p$ is a substituent of one line of Table A Table 28
Compounds of the general formula I.2 where $R^4$ is hydrogen, $R^5X$ is ethyl and $R^x_p$ is a substituent of one line of Table A Table 29
Compounds of the general formula I.1 where $R^4$ is hydrogen, $R^5X$ is methoxy and $R^x_p$ is a substituent of one line of Table A Table 30
Compounds of the general formula I.2 where $R^4$ is hydrogen, $R^5X$ is methoxy and $R^x_p$ is a substituent of one line of Table A Table 31
Compounds of the general formula I.1 where $R^4$ is hydrogen, $R^5X$ is methylamino and $R^x_p$ is a substituent of one line of Table A Table 32
Compounds of the general formula I.2 where $R^4$ is hydrogen, $R^5X$ is methylamino and $R^x_p$ is a substituent of one line of Table A Table 33
Compounds of the general formula I.3 where $R^4$ is hydrogen, $R^5X$ is methyl, $R^y$ is hydrogen, $R^z$ is chlorine and $R^x_p$ is a substituent of one line of Table A Table 34
Compounds of the general formula I.3 where $R^4$ is hydrogen, $R^5X$ is ethyl, $R^y$ is hydrogen, $R^z$ is chlorine and $R^x_p$ is a substituent of one line of Table A Table 35
Compounds of the general formula I.3 where $R^4$ is hydrogen, $R^5X$ is methoxy, $R^y$ is hydrogen, $R^z$ is chlorine and $R^x_p$ is a substituent of one line of Table A Table 36
Compounds of the general formula I.3 where $R^4$ is hydrogen, $R^5X$ is methylamino, $R^y$ is hydrogen, $R^z$ is chlorine and $R^x_p$ is a substituent of one line of Table A Table 37
Compounds of the general formula I.3 where $R^4$ is hydrogen, $R^5X$ is methyl, $R^y$ is methyl, $R^z$ is hydrogen and $R^x_p$ is a substituent of one line of Table A Table 38
Compounds of the general formula I.3 where $R^4$ is hydrogen, $R^5X$ is ethyl, $R^y$ is methyl, $R^z$ is hydrogen and $R^x_p$ is a substituent of one line of Table A Table 39
Compounds of the general formula I.3 where $R^4$ is hydrogen, $R^5X$ is methoxy, $R^y$ is methyl, $R^z$ is hydrogen and $R^x_p$ is a substituent of one line of Table A Table 40
Compounds of the general formula I.3 where $R^4$ is hydrogen, $R^5X$ is methylamino, $R^y$ is methyl, $R^z$ is hydrogen and $R^x_p$ is a substituent of one line of Table A Table 41
Compounds of the general formula I.3 where $R^4$ is hydrogen, $R^5X$ is methyl, $R^y$ is trifluoromethyl, $R^z$ is hydrogen and $R^x_p$ is a substituent of one line of Table A Table 42
Compounds of the general formula I.3 where $R^4$ is hydrogen, $R^5X$ is ethyl, $R^y$ is trifluoromethyl, $R^z$ is hydrogen and $R^x_p$ is a substituent of one line of Table A Table 43
Compounds of the general formula I.3 where $R^4$ is hydrogen, $R^5X$ is methoxy, $R^y$ is trifluoromethyl, $R^z$ is hydrogen and $R^x_p$ is a substituent of one line of Table A Table 44
Compounds of the general formula I.3 where $R^4$ is hydrogen, $R^5X$ is methylamino, $R^y$ is trifluoromethyl, $R^z$ is hydrogen and $R^x_p$ is a substituent of one line of Table A

TABLE A

| Number | $R^x_p$ |
|---|---|
| 1 | H |
| 2 | 2-F |
| 3 | 3-F |
| 4 | 4-F |
| 5 | 2,4-F$_2$ |
| 6 | 2,4,6-F$_3$ |
| 7 | 2,3,4,5,6-F$_5$ |
| 8 | 2,3-F$_2$ |
| 9 | 2-Cl |
| 10 | 3-Cl |
| 11 | 4-Cl |
| 12 | 2,3-Cl$_2$ |
| 13 | 2,4-Cl$_2$ |
| 14 | 2,5-Cl$_2$ |
| 15 | 2,6-Cl$_2$ |
| 16 | 3,4-Cl$_2$ |
| 17 | 3,5-Cl$_2$ |
| 18 | 2,3,4-Cl$_3$ |
| 19 | 2,3,5-Cl$_3$ |
| 11 | 2,3,6-Cl$_3$ |
| 12 | 2,4,5-Cl$_3$ |
| 13 | 2,4,6-Cl$_3$ |
| 14 | 3,4,5-Cl$_3$ |
| 15 | 2,3,4,6-Cl$_4$ |
| 16 | 2,3,5,6-Cl$_4$ |
| 17 | 2,3,4,5,6-Cl$_5$ |
| 18 | 2-Br |
| 19 | 3-Br |
| 20 | 4-Br |
| 21 | 2,4-Br$_2$ |
| 22 | 2,5-Br$_2$ |
| 23 | 2,6-Br$_2$ |
| 24 | 2,4,6-Br$_3$ |
| 25 | 2,3,4,5,6-Br$_5$ |
| 26 | 2-I |
| 27 | 3-I |
| 28 | 4-I |
| 29 | 2,4-I$_2$ |
| 30 | 2-Cl, 3-F |
| 31 | 2-Cl, 4-F |
| 32 | 2-Cl, 5-F |
| 33 | 2-Cl, 6-F |
| 34 | 2-Cl, 3-Br |
| 35 | 2-Cl, 4-Br |
| 36 | 2-Cl, 5-Br |
| 37 | 2-Cl, 6-Br |
| 38 | 2-Br, 3-Cl |
| 39 | 2-Br, 4-Cl |
| 40 | 2-Br, 5-Cl |
| 41 | 2-Br, 3-F |
| 42 | 2-Br, 4-F |
| 43 | 2-Br, 5-F |
| 44 | 2-Br, 6-F |
| 45 | 2-F, 3-Cl |
| 46 | 2-F, 4-Cl |
| 47 | 2-F, 5-Cl |
| 48 | 3-Cl, 4-F |
| 49 | 3-Cl, 5-F |
| 50 | 3-Cl, 4-Br |
| 51 | 3-Cl, 5-Br |
| 52 | 3-F, 4-Cl |
| 53 | 3-F, 4-Br |
| 54 | 3-Br, 4-Cl |
| 55 | 3-Br, 4-F |
| 56 | 2,6-Cl$_2$, 4-Br |
| 57 | 2-CH$_3$ |
| 58 | 3-CH$_3$ |
| 59 | 4-CH$_3$ |
| 60 | 2,3-(CH$_3$)$_2$ |
| 61 | 2,4-(CH$_3$)$_2$ |
| 62 | 2,5-(CH$_3$)$_2$ |
| 63 | 2,6-(CH$_3$)$_2$ |
| 64 | 3,4-(CH$_3$)$_2$ |
| 65 | 3,5-(CH$_3$)$_2$ |
| 66 | 2,3,5-(CH$_3$)$_3$ |
| 67 | 2,3,4-(CH$_3$)$_3$ |
| 68 | 2,3,6-(CH$_3$)$_3$ |
| 69 | 2,4,5-(CH$_3$)$_3$ |
| 70 | 2,4,6-(CH$_3$)$_3$ |
| 71 | 3,4,5-(CH$_3$)$_3$ |
| 72 | 2,3,4,6-(CH$_3$)$_4$ |
| 73 | 2,3,5,6-(CH$_3$)$_4$ |
| 74 | 2,3,4,5,6-(CH$_3$)$_5$ |
| 75 | 2-C$_2$H$_5$ |
| 76 | 3-C$_2$H$_5$ |
| 77 | 4-C$_2$H$_5$ |
| 78 | 2,4-(C$_2$H$_5$)$_5$ |
| 79 | 2,6-(C$_2$H$_5$)$_2$ |
| 80 | 3,5-(C$_2$H$_5$)$_2$ |
| 81 | 2,4,6-(C$_2$H$_5$)$_3$ |
| 82 | 2-n-C$_3$H$_7$ |
| 83 | 3-n-C$_3$H$_7$ |
| 84 | 4-n-C$_3$H$_7$ |
| 85 | 2-i-C$_3$H$_7$ |
| 86 | 3-i-C$_3$H$_7$ |
| 87 | 4-i-C$_3$H$_7$ |
| 88 | 2,4-(i-C$_3$H$_7$)$_2$ |
| 89 | 2,6-(i-C$_3$H$_7$)$_2$ |
| 90 | 3,5-(i-C$_3$H$_7$)$_2$ |
| 91 | 2-5-C$_4$H$_9$ |
| 92 | 3-s-C$_4$H$_9$ |
| 93 | 4-s-C$_4$H$_9$ |
| 94 | 2-t-C$_4$H$_9$ |
| 95 | 3-t-C$_4$H$_9$ |
| 96 | 4-t-C$_4$H$_9$ |
| 97 | 4-n-C$_9$H$_{19}$ |
| 98 | 2-CH$_3$, 4-t-C$_4$H$_9$ |
| 99 | 2-CH$_3$, 6-t-C$_4$H$_9$ |
| 100 | 2-CH$_3$, 4-i-C$_3$H$_7$ |
| 101 | 2-CH$_3$, 5-i-C$_3$H$_7$ |
| 102 | 3-CH$_3$, 4-i-C$_3$H$_7$ |
| 103 | 2-cyclo-C$_6$H$_{11}$ |
| 104 | 3-cyclo-C$_6$H$_{11}$ |
| 105 | 4-cyclo-C$_6$H$_{11}$ |
| 106 | 2-Cl, 4-C$_6$H$_5$ |
| 107 | 2-Br, 4-C$_6$H$_5$ |
| 108 | 2-OCH$_3$ |
| 109 | 3-OCH$_3$ |
| 110 | 4-OCH$_3$ |
| 111 | 2-OC$_2$H$_5$ |
| 112 | 3-O-C$_2$H$_5$ |
| 113 | 4-O-C$_2$H$_5$ |
| 114 | 2-O-n-C$_3$H$_7$ |
| 115 | 3-O-n-C$_3$H$_7$ |
| 116 | 4-O-n-C$_3$H$_7$ |
| 117 | 2-O-i-C$_3$H$_7$ |
| 118 | 3-O-i-C$_3$H$_7$ |
| 119 | 4-O-i-C$_3$H$_7$ |
| 120 | 2-O-n-C$_6$H$_{13}$ |
| 121 | 3-O-n-C$_6$H$_{13}$ |
| 122 | 4-O-n-C$_6$H$_{13}$ |
| 123 | 2-O-CH$_2$C$_6$H$_5$ |
| 124 | 3-O-CH$_2$C$_6$H$_5$ |
| 125 | 4-O-CH$_2$C$_6$H$_5$ |
| 126 | 2-O-(CH$_2$)$_3$C$_6$H$_5$ |
| 127 | 4-O-(CH$_2$)$_3$C$_6$H$_5$ |
| 128 | 2,3-(OCH$_3$)$_2$ |
| 129 | 2,4-(OCH$_3$)$_2$ |
| 130 | 2,5-(OCH$_3$)$_2$ |
| 131 | 2,6-(OCH$_3$)$_2$ |
| 132 | 3,4-(OCH$_3$)$_2$ |
| 133 | 3,5-(OCH$_3$)$_2$ |
| 134 | 2-O-t-C$_4$H$_9$ |
| 135 | 3-O-t-C$_4$H$_9$ |

TABLE A-continued

| Number | $R^x_p$ |
|---|---|
| 136 | 4-O-t-$C_4H_9$ |
| 137 | 3-(3'-Cl—$C_6H_4$) |
| 138 | 4-(4'-$CH_3$—$C_6H_4$) |
| 139 | 2-O—$C_6H_5$ |
| 140 | 3-O—$C_6H_5$ |
| 141 | 4-O—$C_6H_5$ |
| 142 | 2-O-(2'-F—$C_6H_4$) |
| 143 | 3-O-(3'-Cl—$C_6H_4$) |
| 144 | 4-O-(4'-$CH_3$—$C_6H_4$) |
| 145 | 2,3,6-$(CH_3)_3$, 4-F |
| 146 | 2,3,6-$(CH_3)_3$, 4-Cl |
| 147 | 2,3,6-$(CH_3)_3$, 4-Br |
| 148 | 2,4-$(CH_3)_2$, 6-F |
| 149 | 2,4-$(CH_3)_2$, 6-Cl |
| 150 | 2,4-$(CH_3)_2$, 6-Br |
| 151 | 2-i-$C_3H_7$, 4-Cl, 5-$CH_3$ |
| 152 | 2-Cl, 4-$NO_2$ |
| 153 | 2-$NO_2$, 4-Cl |
| 154 | 2-$OCH_3$, 5-$NO_2$ |
| 155 | 2,4-$Cl_2$, 5-$NO_2$ |
| 156 | 2,4-$Cl_2$, 6-$NO_2$ |
| 157 | 2,6-$Cl_2$, 4-$NO_2$ |
| 158 | 2,6-$Br_2$, 4-$NO_2$ |
| 159 | 2,6-$I_2$, 4-$NO_2$ |
| 160 | 2-$CH_3$, 5-i-$C_3H_7$, 4-Cl |
| 161 | 2-$CO_2CH_3$ |
| 162 | 3-$CO_2CH_3$ |
| 163 | 4-$CO_2CH_3$ |
| 164 | 2-$CH_2$-$OCH_3$ |
| 165 | 3-$CH_2$-$OCH_3$ |
| 166 | 4-$CH_2$-$OCH_3$ |
| 167 | 2-Me-4-$CH_3$—$CH(CH_3)$—CO |
| 168 | 2-$CH_3$-4-($CH_3$—C=$NOCH_3$) |
| 169 | 2-$CH_3$-4-($CH_3$—C=$NOC_2H_5$) |
| 170 | 2-$CH_3$-4-($CH_3$—C=NO-n-$C_3H_7$) |
| 171 | 2-$CH_3$-4-($CH_3$—C=NO-i-$C_3H_7$) |
| 172 | 2,5-$(CH_3)_2$-4-($CH_3$—C=$NOCH_3$) |
| 173 | 2,5-$(CH_3)_2$-4-($CH_3$—C=$NOC_2H_5$) |
| 174 | 2,5-$(CH_3)$-4-($CH_3$—C=NO-n-$C_3H_7$) |
| 175 | 2,5-$(CH_3)$-4-($CH_3$—C=NO-i-$C_3H_7$) |
| 176 | 2-$C_6H_5$ |
| 177 | 3-$C_6H_5$ |
| 178 | 4-$C_6H_5$ |
| 179 | 2-(2'-F—$C_6H_4$) |
| 180 | 2-$CH_3$, 5-Br |
| 181 | 2-$CH_3$, 6-Br |
| 182 | 2-Cl, 3-$CH_3$ |
| 183 | 2-Cl, 4-$CH_3$ |
| 184 | 2-Cl, 5-$CH_3$ |
| 185 | 2-F, 3-$CH_3$ |
| 186 | 2-F, 4-$CH_3$ |
| 187 | 2-F, 5-$CH_3$ |
| 188 | 2-Br, 3-$CH_3$ |
| 189 | 2-Br, 4-$CH_3$ |
| 190 | 2-Br, 5-$CH_3$ |
| 191 | 3-$CH_3$, 4-Cl |
| 192 | 3-$CH_3$, 5-Cl |
| 193 | 3-$CH_3$, 4-F |
| 194 | 3-$CH_3$, 5-F |
| 195 | 3-$CH_3$, 4-Br |
| 196 | 3-$CH_3$, 5-Br |
| 197 | 3-F, 4-$CH_3$ |
| 198 | 3-Cl, 4-$CH_3$ |
| 199 | 3-Br, 4-$CH_3$ |
| 200 | 2-Cl, 4,5-$(CH_3)_2$ |
| 201 | 2-Br, 4,5-$(CH_3)_2$ |
| 202 | 2-Cl, 3,5-$(CH_3)_2$ |
| 203 | 2-Br, 3,5-$(CH_3)_2$ |
| 204 | 2,6-$Cl_2$, 4-$CH_3$ |
| 205 | 2,6-$F_2$, 4-$CH_3$ |
| 206 | 2,6-$Br_2$, 4-$CH_3$ |
| 207 | 2,4-$Br_2$, 6-$CH_3$ |
| 208 | 2,4-$F_2$, 6-$CH_3$ |
| 209 | 2,4-$Br_2$, 6-$CH_3$ |
| 210 | 2,6-$(CH_3)_2$, 4-F |
| 211 | 2,6-$(CH_3)_2$, 4-Cl |
| 212 | 2,6-$(CH_3)_2$, 4-Br |
| 213 | 3,5-$(CH_3)_2$, 4-F |
| 214 | 3,5-$(CH_3)_2$, 4-Cl |
| 215 | 3,5-$(CH_3)_2$, 4-Br |
| 216 | 2-$CF_3$ |
| 217 | 3-$CF_3$ |
| 218 | 4-$CF_3$ |
| 219 | 2-$OCF_3$ |
| 220 | 3-$OCF_3$ |
| 221 | 4-$OCF_3$ |
| 222 | 3-$OCH_2CHF_2$ |
| 223 | 2-$NO_2$ |
| 224 | 3-$NO_2$ |
| 225 | 4-$NO_2$ |
| 226 | 2-CN |
| 227 | 3-CN |
| 228 | 4-CN |
| 229 | 2-$CH_3$, 3-Cl |
| 230 | 2-$CH_3$, 4-Cl |
| 231 | 2-$CH_3$, 5-Cl |
| 232 | 2-$CH_3$, 6-Cl |
| 233 | 2-$CH_3$, 3-F |
| 234 | 2-$CH_3$, 4-F |
| 235 | 2-$CH_3$, 5-F |
| 236 | 2-$CH_3$, 6-F |
| 237 | 2-$CH_3$, 3-Br |
| 238 | 2-$CH_3$, 4-Br |
| 239 | 2-Pyridyl-2' |
| 240 | 3-Pyridyl-3' |
| 241 | 4-Pyridyl-4' |

TABLE B

| Number | $R^1$ | $R^y$ | $R^z$ | $R^3$ | $R^4$ |
|---|---|---|---|---|---|
| 1 | H | H | H | Cyclohexyl | $CH_3$ |
| 2 | H | H | H | Benzyl | $CH_3$ |
| 3 | H | H | H | 2-Pyridyl | $CH_3$ |
| 4 | H | H | H | 5-Cl-pyridyl-2 | $CH_3$ |
| 5 | H | H | H | 5-$CF_3$-pyridyl-2 | $CH_3$ |
| 6 | H | H | H | 2-Pyrazinyl | $CH_3$ |
| 7 | H | H | Cl | Cyclohexyl | $CH_3$ |
| 8 | H | H | Cl | Benzyl | $CH_3$ |
| 9 | H | H | Cl | 2-Pyridyl | $CH_3$ |
| 10 | H | H | Cl | 5-Cl-pyridyl-2 | $CH_3$ |
| 11 | H | H | Cl | 5-$CF_3$-pyridyl-2 | $CH_3$ |
| 12 | H | H | Cl | 2-Pyrazinyl | $CH_3$ |
| 13 | H | $CH_3$ | H | Cyclohexyl | $CH_3$ |
| 14 | H | $CH_3$ | H | Benzyl | $CH_3$ |
| 15 | H | $CH_3$ | H | 2-Pyridyl | $CH_3$ |
| 16 | H | $CH_3$ | H | 5-Cl-pyridyl-2 | $CH_3$ |
| 17 | H | $CH_3$ | H | 5-$CF_3$-pyridyl-2 | $CH_3$ |
| 18 | H | $CH_3$ | H | 2-Pyrazinyl | $CH_3$ |
| 19 | H | H | H | Cyclohexyl | $C_2H_5$ |
| 20 | H | H | H | Benzyl | $C_2H_5$ |
| 21 | H | H | H | Phenyl | $C_2H_5$ |
| 22 | H | H | H | 2-Pyridyl | $C_2H_5$ |
| 23 | H | H | H | 5-Cl-pyridyl-2 | $C_2H_5$ |
| 24 | H | H | H | 5-$CF_3$-pyridyl-2 | $C_2H_5$ |
| 25 | H | H | H | 2-Pyrazinyl | $C_2H_5$ |
| 26 | H | H | Cl | Cyclohexyl | $C_2H_5$ |
| 27 | H | H | Cl | Benzyl | $C_2H_5$ |
| 28 | H | H | Cl | Phenyl | $C_2H_5$ |
| 29 | H | H | Cl | 2-Pyridyl | $C_2H_5$ |
| 30 | H | H | Cl | 5-Cl-pyridyl-2 | $C_2H_5$ |
| 31 | H | H | Cl | 5-$CF_3$-pyridyl-2 | $C_2H_5$ |
| 32 | H | H | Cl | 2-Pyrazinyl | $C_2H_5$ |
| 33 | H | $CH_3$ | H | Cyclohexyl | $C_2H_5$ |
| 34 | H | $CH_3$ | H | Benzyl | $C_2H_5$ |
| 35 | H | $CH_3$ | H | Phenyl | $C_2H_5$ |
| 36 | H | $CH_3$ | H | 2-Pyridyl | $C_2H_5$ |
| 37 | H | $CH_3$ | H | 5-Cl-pyridyl-2 | $C_2H_5$ |
| 38 | H | $CH_3$ | H | 5-$CF_3$-pyridyl-2 | $C_2H_5$ |
| 39 | H | $CH_3$ | H | 2-Pyrazinyl | $C_2H_5$ |
| 40 | H | H | H | Cyclohexyl | $CH_2OCH_3$ |

TABLE B-continued

| Number | R¹ | $R^y$ | $R^z$ | R³ | R⁴ |
|---|---|---|---|---|---|
| 41 | H | H | H | Benzyl | CH₂OCH₃ |
| 42 | H | H | H | Phenyl | CH₂OCH₃ |
| 43 | H | H | H | 2-Pyridyl | CH₂OCH₃ |
| 44 | H | H | H | 5-Cl-pyridyl-2 | CH₂OCH₃ |
| 45 | H | H | H | 5-CF₃-pyridyl-2 | CH₂OCH₃ |
| 46 | H | H | H | 2-Pyrazinyl | CH₂OCH₃ |
| 47 | H | H | Cl | Cyclohexyl | CH₂OCH₃ |
| 48 | H | H | Cl | Benzyl | CH₂OCH₃ |
| 49 | H | H | Cl | Phenyl | CH₂OCH₃ |
| 50 | H | H | Cl | 2-Pyridyl | CH₂OCH₃ |
| 51 | H | H | Cl | 5-Cl-pyridyl-2 | CH₂OCH₃ |
| 52 | H | H | Cl | 5-CF₃-pyridyl-2 | CH₂OCH₃ |
| 53 | H | H | Cl | 2-Pyrazinyl | CH₂OCH₃ |
| 54 | H | CH₃ | H | Cyclohexyl | CH₂OCH₃ |
| 55 | H | CH₃ | H | Benzyl | CH₂OCH₃ |
| 56 | H | CH₃ | H | Phenyl | CH₂OCH₃ |
| 57 | H | CH₃ | H | 2-Pyridyl | CH₂OCH₃ |
| 58 | H | CH₃ | H | 5-Cl-pyridyl-2 | CH₂OCH₃ |
| 59 | H | CH₃ | H | 5-CF₃-pyridyl-2 | CH₂OCH₃ |
| 60 | H | CH₃ | H | 2-Pyrazinyl | CH₂OCH₃ |
| 61 | H | H | H | Cyclohexyl | CH₂C≡CH |
| 62 | H | H | H | Benzyl | CH₂C≡CH |
| 63 | H | H | H | Phenyl | CH₂C≡CH |
| 64 | H | H | H | 2-Pyridyl | CH₂C≡CH |
| 65 | H | H | H | 5-Cl-pyridyl-2 | CH₂C≡CH |
| 66 | H | H | H | 5-CF₃-pyridyl-2 | CH₂C≡CH |
| 67 | H | H | H | 2-Pyrazinyl | CH₂C≡CH |
| 68 | H | H | Cl | Cyclohexyl | CH₂C≡CH |
| 69 | H | H | Cl | Benzyl | CH₂C≡CH |
| 70 | H | H | Cl | Phenyl | CH₂C≡CH |
| 71 | H | H | Cl | 2-Pyridyl | CH₂C≡CH |
| 72 | H | H | Cl | 5-Cl-pyridyl-2 | CH₂C≡CH |
| 73 | H | H | Cl | 5-CF₃-pyridyl-2 | CH₂C≡CH |
| 74 | H | H | Cl | 2-Pyrazinyl | CH₂C≡CH |
| 75 | H | CH₃ | H | Cyclohexyl | CH₂C≡CH |
| 76 | H | CH₃ | H | Benzyl | CH₂C≡CH |
| 77 | H | CH₃ | H | Phenyl | CH₂C≡CH |
| 78 | H | CH₃ | H | 2-Pyridyl | CH₂C≡CH |
| 79 | H | CH₃ | H | 5-Cl-pyridyl-2 | CH₂C≡CH |
| 80 | H | CH₃ | H | 5-CF₃-pyridyl-2 | CH₂C≡CH |
| 81 | H | CH₃ | H | 2-Pyrazinyl | CH₂C≡CH |
| 82 | 3-F | H | H | Cyclohexyl | CH₃ |
| 83 | 3-F | H | H | Benzyl | CH₃ |
| 84 | 3-F | H | H | Phenyl | CH₃ |
| 85 | 3-F | H | H | 2-Pyridyl | CH₃ |
| 86 | 3-F | H | H | 5-Cl-pyridyl-2 | CH₃ |
| 87 | 3-F | H | H | 5-CF₃-pyridyl-2 | CH₃ |
| 88 | 3-F | H | H | 2-Pyrazinyl | CH₃ |
| 89 | 3-F | H | Cl | Cyclohexyl | CH₃ |
| 90 | 3-F | H | Cl | Benzyl | CH₃ |
| 91 | 3-F | H | Cl | Phenyl | CH₃ |
| 92 | 3-F | H | Cl | 2-Pyridyl | CH₃ |
| 93 | 3-F | H | Cl | 5-Cl-pyridyl-2 | CH₃ |
| 94 | 3-F | H | Cl | 5-CF₃-pyridyl-2 | CH₃ |
| 95 | 3-F | H | Cl | 2-Pyrazinyl | CH₃ |
| 96 | 3-F | CH₃ | H | Cyclohexyl | CH₃ |
| 97 | 3-F | CH₃ | H | Benzyl | CH₃ |
| 98 | 3-F | CH₃ | H | Phenyl | CH₃ |
| 99 | 3-F | CH₃ | H | 2-Pyridyl | CH₃ |
| 100 | 3-F | CH₃ | H | 5-Cl-pyridyl-2 | CH₃ |
| 101 | 3-F | CH₃ | H | 5-CF₃-pyridyl-2 | CH₃ |
| 102 | 3-F | CH₃ | H | 2-Pyrazinyl | CH₃ |
| 103 | 3-F | H | H | Cyclohexyl | C₂H₅ |
| 104 | 3-F | H | H | Benzyl | C₂H₅ |
| 105 | 3-F | H | H | Phenyl | C₂H₅ |
| 106 | 3-F | H | H | 2-Pyridyl | C₂H₅ |
| 107 | 3-F | H | H | 5-Cl-pyridyl-2 | C₂H₅ |
| 108 | 3-F | H | H | 5-CF₃-pyridyl-2 | C₂H₅ |
| 109 | 3-F | H | H | 2-Pyrazinyl | C₂H₅ |
| 110 | 3-F | H | Cl | Cyclohexyl | C₂H₅ |
| 111 | 3-F | H | Cl | Benzyl | C₂H₅ |
| 112 | 3-F | H | Cl | Phenyl | C₂H₅ |
| 113 | 3-F | H | Cl | 2-Pyridyl | C₂H₅ |
| 114 | 3-F | H | Cl | 5-Cl-pyridyl-2 | C₂H₅ |
| 115 | 3-F | H | Cl | 5-CF₃-pyridyl-2 | C₂H₅ |
| 116 | 3-F | H | Cl | 2-Pyrazinyl | C₂H₅ |
| 117 | 3-F | H | H | Cyclohexyl | CH₂OCH₃ |
| 118 | 3-F | H | H | Benzyl | CH₂OCH₃ |
| 119 | 3-F | H | H | Phenyl | CH₂OCH₃ |
| 120 | 3-F | H | H | 2-Pyridyl | CH₂OCH₃ |
| 121 | 3-F | H | H | 5-Cl-pyridyl-2 | CH₂OCH₃ |
| 122 | 3-F | H | H | 5-CF₃-pyridyl-2 | CH₂OCH₃ |
| 123 | 3-F | H | H | 2-Pyrazinyl | CH₂OCH₃ |
| 124 | 3-F | H | Cl | Cyclohexyl | CH₂OCH₃ |
| 125 | 3-F | H | Cl | Benzyl | CH₂OCH₃ |
| 126 | 3-F | H | Cl | Phenyl | CH₂OCH₃ |
| 127 | 3-F | H | Cl | 2-Pyridyl | CH₂OCH₃ |
| 128 | 3-F | H | Cl | 5-Cl-pyridyl-2 | CH₂OCH₃ |
| 129 | 3-F | H | Cl | 5-CF₃-pyridyl-2 | CH₂OCH₃ |
| 130 | 3-F | H | Cl | 2-Pyrazinyl | CH₂OCH₃ |
| 131 | 3-F | CH₃ | H | Cyclohexyl | CH₂OCH₃ |
| 132 | 3-F | CH₃ | H | Benzyl | CH₂OCH₃ |
| 133 | 3-F | CH₃ | H | Phenyl | CH₂OCH₃ |
| 134 | 3-F | CH₃ | H | 2-Pyridyl | CH₂OCH₃ |
| 135 | 3-F | CH₃ | H | 5-Cl-pyridyl-2 | CH₂OCH₃ |
| 136 | 3-F | CH₃ | H | 5-CF₃-pyridyl-2 | CH₂OCH₃ |
| 137 | 3-F | CH₃ | H | 2-Pyrazinyl | CH₂OCH₃ |
| 138 | 3-F | H | H | Cyclohexyl | CH₂C≡CH |
| 139 | 3-F | H | H | Benzyl | CH₂C≡CH |
| 140 | 3-F | H | H | Phenyl | CH₂C≡CH |
| 141 | 3-F | H | H | 2-Pyridyl | CH₂C≡CH |
| 142 | 3-F | H | H | 5-Cl-pyridyl-2 | CH₂C≡CH |
| 143 | 3-F | H | H | 5-CF₃-pyridyl-2 | CH₂C≡CH |
| 144 | 3-F | H | H | 2-Pyrazinyl | CH₂C≡CH |
| 145 | 3-F | H | Cl | Cyclohexyl | CH₂C≡CH |
| 146 | 3-F | H | Cl | Benzyl | CH₂C≡CH |
| 147 | 3-F | H | Cl | Phenyl | CH₂C≡CH |
| 148 | 3-F | H | Cl | 2-Pyridyl | CH₂C≡CH |
| 149 | 3-F | H | Cl | 5-Cl-pyridyl-2 | CH₂C≡CH |
| 150 | 3-F | H | Cl | 5-CF3-pyridyl-2 | CH₂C≡CH |
| 151 | 3-F | H | Cl | 2-Pyrazinyl | CH₂C≡CH |
| 152 | 3-F | CH₃ | H | Cyclohexyl | CH₂C≡CH |
| 153 | 3-F | CH₃ | H | Benzyl | CH₂C≡CH |
| 154 | 3-F | CH₃ | H | Phenyl | CH₂C≡CH |
| 155 | 3-F | CH₃ | H | 2-Pyridyl | CH₂C≡CH |
| 156 | 3-F | CH₃ | H | 5-Cl-pyridyl-2 | CH₂C≡CH |
| 157 | 3-F | CH₃ | H | 5-CF₃-pyridyl-2 | CH₂C≡CH |
| 158 | 3-F | CH₃ | H | 2-Pyrazinyl | CH₂C≡CH |
| 159 | 6-Cl | H | H | Cyclohexyl | CH₃ |
| 160 | 6-Cl | H | H | Benzyl | CH₃ |
| 161 | 6-Cl | H | H | Phenyl | CH₃ |
| 162 | 6-Cl | H | H | 2-Pyridyl | CH₃ |
| 163 | 6-Cl | H | H | 5-Cl-pyridyl-2 | CH₃ |
| 164 | 6-Cl | H | H | 5-CF₃-pyridyl-2 | CH₃ |
| 165 | 6-Cl | H | H | 2-Pyrazinyl | CH₃ |
| 166 | 6-Cl | H | Cl | Cyclohexyl | CH₃ |
| 167 | 6-Cl | H | Cl | Benzyl | CH₃ |
| 166 | 6-Cl | H | Cl | Phenyl | CH₃ |
| 169 | 6-Cl | H | Cl | 2-Pyridyl | CH₃ |
| 170 | 6-Cl | H | Cl | 5-Cl-pyridyl-2 | CH₃ |
| 171 | 6-Cl | H | Cl | 5-CF₃-pyridyl-2 | CH₃ |
| 172 | 6-Cl | H | Cl | 2-Pyrazinyl | CH₃ |
| 173 | 6-Cl | CH₃ | H | Cyclohexyl | CH₃ |
| 174 | 6-Cl | CH₃ | H | Benzyl | CH₃ |
| 175 | 6-Cl | CH₃ | H | Phenyl | CH₃ |
| 176 | 6-Cl | CH₃ | H | 2-Pyridyl | CH₃ |
| 177 | 6-Cl | CH₃ | H | 5-Cl-pyridyl-2 | CH₃ |
| 178 | 6-Cl | CH₃ | H | 5-CF₃-pyridyl-2 | CH₃ |
| 179 | 6-Cl | CH₃ | H | 2-Pyrazinyl | CH₃ |
| 180 | 6-Cl | H | H | Cyclohexyl | C₂H₅ |
| 161 | 6-Cl | H | H | Benzyl | C₂H₅ |
| 182 | 6-Cl | H | H | Phenyl | C₂H₅ |
| 183 | 6-Cl | H | H | 2-Pyridyl | C₂H₅ |
| 184 | 6-Cl | H | H | 5-Cl-pyridyl-2 | C₂H₅ |
| 185 | 6-Cl | H | H | 5-CF₃-pyridyl-2 | C₂H₅ |
| 186 | 6-Cl | H | H | 2-Pyrazinyl | C₂H₅ |
| 187 | 6-Cl | H | Cl | Cyclohexyl | C₂H₅ |
| 188 | 6-Cl | H | Cl | Benzyl | C₂H₅ |
| 189 | 6-Cl | H | Cl | Phenyl | C₂H₅ |
| 190 | 6-Cl | H | Cl | 2-Pyridyl | C₂H₅ |
| 191 | 6-Cl | H | Cl | 5-Cl-pyridyl-2 | C₂H₅ |
| 192 | 6-Cl | H | Cl | 5-CF₃-pyridyl-2 | C₂H₅ |
| 193 | 6-Cl | H | Cl | 2-Pyrazinyl | C₂H₅ |
| 194 | 6-Cl | CH₃ | H | Cyclohexyl | C₂H₅ |

TABLE B-continued

| Number | R¹ | Rʸ | Rᶻ | R³ | R⁴ |
|---|---|---|---|---|---|
| 195 | 6-Cl | CH₃ | H | Benzyl | C₂H₅ |
| 196 | 6-Cl | CH₃ | H | Phenyl | C₂H₅ |
| 197 | 6-Cl | CH₃ | H | 2-Pyridyl | C₂H₅ |
| 198 | 6-Cl | CH₃ | H | 5-Cl-pyridyl-2 | C₂H₅ |
| 199 | 6-Cl | CH₃ | H | 5-CF₃-pyridyl-2 | C₂H₅ |
| 200 | 6-Cl | CH₃ | H | 2-Pyrazinyl | C₂H₅ |
| 201 | 6-Cl | H | H | Cyclohexyl | CH₂OCH₃ |
| 202 | 6-Cl | H | H | Benzyl | CH₂OCH₃ |
| 203 | 6-Cl | H | H | Phenyl | CH₂OCH₃ |
| 204 | 6-Cl | H | H | 2-Pyridyl | CH₂OCH₃ |
| 205 | 6-Cl | H | H | 5-Cl-pyridyl-2 | CH₂OCH₃ |
| 206 | 6-Cl | H | H | 5-CF₃-pyridyl-2 | CH₂OCH₃ |
| 207 | 6-Cl | H | H | 2-Pyrazinyl | CH₂OCH₃ |
| 208 | 6-Cl | H | Cl | Cyclohexyl | CH₂OCH₃ |
| 209 | 6-Cl | H | Cl | Benzyl | CH₂OCH₃ |
| 210 | 6-Cl | H | Cl | Phenyl | CH₂OCH₃ |
| 211 | 6-Cl | H | Cl | 2-Pyridyl | CH₂OCH₃ |
| 212 | 6-Cl | H | Cl | 5-Cl-pyridyl-2 | CH₂OCH₃ |
| 213 | 6-Cl | H | Cl | 5-CF₃-pyridyl-2 | CH₂OCH₃ |
| 214 | 6-Cl | H | Cl | 2-Pyrazinyl | CH₂OCH₃ |
| 215 | 6-Cl | CH₃ | H | Cyclohexyl | CH₂OCH₃ |
| 216 | 6-Cl | CH₃ | H | Benzyl | CH₂OCH₃ |
| 217 | 6-Cl | CH₃ | H | Phenyl | CH₂OCH₃ |
| 218 | 6-Cl | CH₃ | H | 2-Pyridyl | CH₂OCH₃ |
| 219 | 6-Cl | CH₃ | H | 5-Cl-pyridyl-2 | CH₂OCH₃ |
| 220 | 6-Cl | CH₃ | H | 5-CF₃-pyridyl-2 | CH₂OCH₃ |
| 221 | 6-Cl | CH₃ | H | 2-Pyrazinyl | CH₂OCH₃ |
| 222 | 6-Cl | H | H | Cyclohexyl | CH₂C≡CH |
| 223 | 6-Cl | H | H | Benzyl | CH₂C≡CH |
| 224 | 6-Cl | H | H | Phenyl | CH₂C≡CH |
| 225 | 6-Cl | H | H | 2-Pyridyl | CH₂C≡CH |
| 226 | 6-Cl | H | H | 5-Cl-pyridyl-2 | CH₂C≡CH |
| 227 | 6-Cl | H | H | 5-CF₃-pyridyl-2 | CH₂C≡CH |
| 228 | 6-Cl | H | H | 2-Pyrazinyl | CH₂C≡CH |
| 229 | 6-Cl | H | Cl | Cyclohexyl | CH₂C≡CH |
| 230 | 6-Cl | H | Cl | Benzyl | CH₂C≡CH |
| 231 | 6-Cl | H | Cl | Phenyl | CH₂C≡CH |
| 232 | 6-Cl | H | Cl | 2-Pyridyl | CH₂C≡CH |
| 233 | 6-Cl | H | Cl | 5-Cl-pyridyl-2 | CH₂C≡CH |
| 234 | 6-Cl | H | Cl | 5-CF₃-pyridyl-2 | CH₂C≡CH |
| 235 | 6-Cl | H | Cl | 2-Pyrazinyl | CH₂C≡CH |
| 236 | 6-Cl | CH₃ | H | Cyclohexyl | CH₂C≡CH |
| 237 | 6-Cl | CH₃ | H | Benzyl | CH₂C≡CH |
| 238 | 6-Cl | CH₃ | H | Phenyl | CH₂C≡CH |
| 239 | 6-Cl | CH₃ | H | 2-Pyridyl | CH₂C≡CH |
| 240 | 6-Cl | CH₃ | H | 5-Cl-pyridyl-2 | CH₂C≡CH |
| 241 | 6-Cl | CH₃ | H | 5-CF₃-pyridyl-2 | CH₂C≡CH |
| 242 | 6-Cl | CH₃ | H | 2-Pyrazinyl | CH₂C≡CH |
| 243 | 6-CH₃ | H | H | Cyclohexyl | CH₃ |
| 244 | 6-CH₃ | H | H | Benzyl | CH₃ |
| 245 | 6-CH₃ | H | H | Phenyl | CH₃ |
| 246 | 6-CH₃ | H | H | 2-Pyridyl | CH₃ |
| 247 | 6-CH₃ | H | H | 5-Cl-pyridyl-2 | CH₃ |
| 248 | 6-CH₃ | H | H | 5-CF₃-pyridyl-2 | CH₃ |
| 249 | 6-CH₃ | H | H | 2-Pyrazinyl | CH₃ |
| 250 | 6-CH₃ | H | Cl | Cyclohexyl | CH₃ |
| 251 | 6-CH₃ | H | Cl | Benzyl | CH₃ |
| 252 | 6-CH₃ | H | Cl | Phenyl | CH₃ |
| 253 | 6-CH₃ | H | Cl | 2-Pyridyl | CH₃ |
| 254 | 6-CH₃ | H | Cl | 5-Cl-pyridyl-2 | CH₃ |
| 255 | 6-CH₃ | H | Cl | 5-CF₃-pyridyl-2 | CH₃ |
| 256 | 6-CH₃ | H | Cl | 2-Pyrazinyl | CH₃ |
| 257 | 6-CH₃ | CH₃ | H | Cyclohexyl | CH₃ |
| 258 | 6-CH₃ | CH₃ | H | Benzyl | CH₃ |
| 259 | 6-CH₃ | CH₃ | H | Phenyl | CH₃ |
| 260 | 6-CH₃ | CH₃ | H | 2-Pyridyl | CH₃ |
| 261 | 6-CH₃ | CH₃ | H | 5-Cl-pyridyl-2 | CH₃ |
| 262 | 6-CH₃ | CH₃ | H | 5-CF₃-pyridyl-2 | CH₃ |
| 263 | 6-CH₃ | CH₃ | H | 2-Pyrazinyl | CH₃ |
| 264 | 6-CH₃ | H | H | Cyclohexyl | C₂H₅ |
| 265 | 6-CH₃ | H | H | Benzyl | C₂H₅ |
| 266 | 6-CH₃ | H | H | Phenyl | C₂H₅ |
| 267 | 6-CH₃ | H | H | 2-Pyridyl | C₂H₅ |
| 268 | 6-CH₃ | H | H | 5-Cl-pyridyl-2 | C₂H₅ |
| 269 | 6-CH₃ | H | H | 5-CF₃-pyridyl-2 | C₂H₅ |
| 270 | 6-CH₃ | H | H | 2-Pyrazinyl | C₂H₅ |
| 271 | 6-CH₃ | H | Cl | Cyclohexyl | C₂H₅ |
| 272 | 6-CH₃ | H | Cl | Benzyl | C₂H₅ |
| 273 | 6-CH₃ | H | Cl | Phenyl | C₂H₅ |
| 274 | 6-CH₃ | H | Cl | 2-Pyridyl | C₂H₅ |
| 275 | 6-CH₃ | H | Cl | 5-Cl-pyridyl-2 | C₂H₅ |
| 276 | 6-CH₃ | H | Cl | 5-CF₃-pyridyl-2 | C₂H₅ |
| 277 | 6-CH₃ | H | Cl | 2-Pyrazinyl | C₂H₅ |
| 278 | 6-CH₃ | CH₃ | H | Cyclohexyl | C₂H₅ |
| 279 | 6-CH₃ | CH₃ | H | Benzyl | C₂H₅ |
| 280 | 6-CH₃ | CH₃ | H | Phenyl | C₂H₅ |
| 281 | 6-CH₃ | CH₃ | H | 2-Pyridyl | C₂H₅ |
| 282 | 6-CH₃ | CH₃ | H | 5-Cl-pyridyl-2 | C₂H₅ |
| 283 | 6-CH₃ | CH₃ | H | 5-CF₃-pyridyl-2 | C₂H₅ |
| 284 | 6-CH₃ | CH₃ | H | 2-Pyrazinyl | C₂H₅ |
| 285 | 6-CH₃ | H | H | Cyclohexyl | CH₂OCH₃ |
| 286 | 6-CH₃ | H | H | Benzyl | CH₂OCH₃ |
| 287 | 6-CH₃ | H | H | Phenyl | CH₂OCH₃ |
| 288 | 6-CH₃ | H | H | 2-Pyridyl | CH₂OCH₃ |
| 289 | 6-CH₃ | H | H | 5-Cl-pyridyl-2 | CH₂OCH₃ |
| 290 | 6-CH₃ | H | H | 5-CF₃-pyridyl-2 | CH₂OCH₃ |
| 291 | 6-CH₃ | H | H | 2-Pyrazinyl | CH₂OCH₃ |
| 292 | 6-CH₃ | H | Cl | Cyclohexyl | CH₂OCH₃ |
| 293 | 6-CH₃ | H | Cl | Benzyl | CH₂OCH₃ |
| 294 | 6-CH₃ | H | Cl | Phenyl | CH₂OCH₃ |
| 295 | 6-CH₃ | H | Cl | 2-Pyridyl | CH₂OCH₃ |
| 296 | 6-CH₃ | H | Cl | 5-Cl-pyridyl-2 | CH₂OCH₃ |
| 297 | 6-CH₃ | H | Cl | 5-CF₃-pyridyl-2 | CH₂OCH₃ |
| 298 | 6-CH₃ | H | Cl | 2-Pyrazinyl | CH₂OCH₃ |
| 299 | 6-CH₃ | CH₃ | H | Cyclohexyl | CH₂OCH₃ |
| 300 | 6-CH₃ | CH₃ | H | Benzyl | CH₂OCH₃ |
| 301 | 6-CH₃ | CH₃ | H | Phenyl | CH₂OCH₃ |
| 302 | 6-CH₃ | CH₃ | H | 2-Pyridyl | CH₂OCH₃ |
| 303 | 6-CH₃ | CH₃ | H | 5-Cl-pyridyl-2 | CH₂OCH₃ |
| 304 | 6-CH₃ | CH₃ | H | 5-CF₃-pyridyl-2 | CH₂OCH₃ |
| 305 | 6-CH₃ | CH₃ | H | 2-Pyrazinyl | CH₂OCH₃ |
| 306 | 6-CH₃ | H | H | Cyclohexyl | CH₂C≡CH |
| 307 | 6-CH₃ | H | H | Benzyl | CH₂C≡CH |
| 308 | 6-CH₃ | H | H | Phenyl | CH₂C≡CH |
| 309 | 6-CH₃ | H | H | 2-Pyridyl | CH₂C≡CH |
| 310 | 6-CH₃ | H | H | 5-Cl-pyridyl-2 | CH₂C≡CH |
| 311 | 6-CH₃ | H | H | 5-CF₃-pyridyl-2 | CH₂C≡CH |
| 312 | 6-CH₃ | H | H | 2-Pyrazinyl | CH₂C≡CH |
| 313 | 6-CH₃ | H | Cl | Cyclohexyl | CH₂C≡CH |
| 314 | 6-CH₃ | H | Cl | Benzyl | CH₂C≡CH |
| 315 | 6-CH₃ | H | Cl | Phenyl | CH₂C≡CH |
| 316 | 6-CH₃ | H | Cl | 2-Pyridyl | CH₂C≡CH |
| 317 | 6-CH₃ | H | Cl | 5-Cl-pyridyl-2 | CH₂C≡CH |
| 318 | 6-CH₃ | H | Cl | 5-CF₃-pyridyl-2 | CH₂C≡CH |
| 319 | 6-CH₃ | H | Cl | 2-Pyrazinyl | CH₂C≡CH |
| 320 | 6-CH₃ | CH₃ | H | Cyclohexyl | CH₂C≡CH |
| 321 | 6-CH₃ | CH₃ | H | Benzyl | CH₂C≡CH |
| 322 | 6-CH₃ | CH₃ | H | Phenyl | CH₂C≡CH |
| 323 | 6-CH₃ | CH₃ | H | 2-Pyridyl | CH₂C≡CH |
| 324 | 6-CH₃ | CH₃ | H | 5-Cl-pyridyl-2 | CH₂C≡CH |
| 325 | 6-CH₃ | CH₃ | H | 5-CF₃-pyridyl-2 | CH₂C≡CH |
| 326 | 6-CH₃ | CH₃ | H | 2-Pyrazinyl | CH₂C≡CH |
| 327 | 3-F | CH₃ | H | Cyclohexyl | C₂H₅ |
| 328 | 3-F | CH₃ | H | Benzyl | C₂H₅ |
| 329 | 3-F | CH₃ | H | Phenyl | C₂H₅ |
| 330 | 3-F | CH₃ | H | 2-Pyridyl | C₂H₅ |
| 331 | 3-F | CH₃ | H | 5-Cl-pyridyl-2 | C₂H₅ |
| 332 | 3-F | CH₃ | H | 5-CF₃-pyridyl-2 | C₂H₅ |
| 333 | 3-F | CH₃ | H | 2-Pyrazinyl | C₂H₅ |

The compounds of the formula I according to the invention are suitable for controlling harmful fungi and animal pests of the insects, arachnids and nematodes class. They can be employed as fungicides and pesticides in the crop protection and in the hygiene, stored material protection and veterinary sectors.

The harmful insects include:

from the order of the butterflies (Lepidoptera), for example, Adoxophyes orana, Agrotis ypsilon, Agrotis segetum, Alabama argillacea, Anticarsia gemmatalis, Argyresthia conjugella, Autographa gamma, Cacoecia murinana, Capua reticulana, Choristoneura fumiferana, Chilo partellus, Choristoneura occidentalis, Cirphis unipuncta, Cnaphalocrocis medinalis, Crocidolomia binotalis, Cydia pomonella, Dendrolimus pini, Diaphania nitidalis, Diatraea grandiosella, Earias insulana, Elasmopalpus lignosellus, Eupoecilia ambiguella, Feltia subterranea, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera scitella, Lithocolletis blancardella, Lobesia botrana, Loxostege sticticalis, Lymantria dispar, Lymantria monacha, Lyonetia clerkella, Manduca sexta, Malacosoma neustria, Mamestra brassicae, Mocis repanda, Operophthera brumata, Orgyia pseudotsugata, Ostrinia nubilalis, Pandemis heparana, Panolis flammea, Pectinophora gossypiella, Phthorimaea operculella, Phyllocnistis citrella, Pieris brassicae, Plathypena scabra, Platynota stultana, Plutella xylostella, Prays citri, Prays oleae, Prodenia sunia, Prodenia ornithogalli, Pseudoplusia includens, Rhyacionia frustrana, Scrobipalpula absoluta, Sesamia inferens, Sparganothis pilleriana, Spodoptera frugiperda, Spodoptera littoralis, Spodoptera litura, Syllepta derogata, Synanthedon myopaeformis, Thaumatopoea pityocampa, Tortrix viridana, Trichoplusia ni, Tryporyza incertulas, Zeiraphera canadensis, also Galleria mellonella and Sitotroga cerealella, Ephestia cautella, Tineola bisselliella;

from the order of the beetles (Coleoptera), for example, Agriotes lineatus, Agriotes obscurus, Anthonomus grandis, Anthonomus pomorum, Apion vorax, Atomaria linearis, Blastophagus piniperda, Cassida nebulosa, Cerotoma trifurcata, Ceuthorhynchus assimilis, Ceuthorhynchus napi, Chaetocnema tibialis, Conoderus vespertinus, Crioceris asparagi, Dendroctonus refipennis, diabrotica longicornis, diabrotica 12-punctata, diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllopertha horticola, Phyllophaga sp., Phyllotreta chrysocephala, Phyllotreta nemorum, Phyllotreta striolata, Popillia japonica, Psylliodes napi, Scolytus intricatus, Sitona lineatus, also Bruchus rufimanus, Bruchus pisorum, Bruchus lentis, Sitophilus granaria, Lasioderma serricorne, oryzaephilus surinamensis, Rhyzopertha dominica, Sitophilus oryzae, Tribolium castaneum, Trogoderma granarium, Zabrotes subfasciatus;

from the order of the dipterous insects (Diptera), for example, Anastrepha ludens, Ceratitis capitata, Contarinia sorghicola, Dacus cucurbitae, Dacus oleae, Dasineura brassicae, Delia coarctata, Delia radicum, Hydrellia griseola, Hylemyia platura, Liriomyza sativae, Liriomyza trifolii, Mayetiola destructor, Orseolia oryzae, Oscinella frit, Pegomya hyoscyami, Phorbia antiqua, Phorbia brassicae, Phorbia coarctata, Rhagoletis cerasi, Rhagoletis pomonella, Tipula oleracea, Tipula paludosa, also Aedes aegypti, Aedes vexans, Anopheles maculipennis, Chrysomya bezziana, Chrysomya hominivorax, Chrysomya macellaria, Cordylobia anthropophaga, Culex pipiens, Fannia canicularis, Gasterophilus intestinalis, Glossina morsitans, Haematobia irritans, Haplodiplosis equestris, Hypoderma lineata, Lucilia caprina, Lucilia cuprina, Lucilia sericata, Musca domestica, Muscina stabulans, Oestrus ovis, Tabanus bovinus, Simulium damnosum;

from the order of the thrips (Thysanoptera), for example, Frankliniella fusca, Frankliniella occidentalis, Frankliniella tritici, Haplothrips tritici, Scirtothrips citri, Thrips oryzae, Thrips palmi, Thrips tabaci;

from the order of the hymenopterous insects (Hymenoptera), for example, Athalia rosae, Atta cephalotes, Atta sexdens, Atta texana, Hoplocampa minuta, Hoplocampa testudinea, Iridomyrmes humilis, Iridomyrmex purpureus, Monomorium pharaonis, Solenopsis geminata, Solenopsis invicta, Solenopsis richteri;

from the order of the bed bugs (Heteroptera), for example, Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus hesperus, Lygus lineolaris, Lygus pratensis, Nezara viridula, Piesma quadrata, Solubea insularis, Thyanta perditor;

from the order of the plant-sucking insects (Homoptera), for example, Acyrthosiphon onobrychis, Acyrthosiphon pisum, Adelges laricis, Aonidiella aurantii, Aphidula nasturtii, Aphis fabae, Aphis gossypii, Aphis pomi, Aulacorthum solani, Bemisia tabaci, Brachycaudus cardui, Brevicoryne brassicae, Dalbulus maidis, Dreyfusia nordmannianae, Dreyfusia piceae, Dysaphis radicola, Empoasca fabae, Eriosoma lanigerum, Laodelphax striatella, Macrosiphum avenae, Macrosiphum euphorbiae, Macrosiphon rosae, egoura viciae, Metopolophium dirhodum, Myzus persicae, Myzus cerasi, Nephotettix cincticeps, Nilaparvata lugens, Perkinsiella saccharicida, Phorodon humuli, Planococcus citri, Psylla mali, Psylla piri, Psylla pyricol, Quadraspidiotus perniciosus, Rhopalosiphum maidis, Saissetia oleae, Schizaphis graminum, Selenaspidus articulatus, Sitobion avenae, Sogatella furcifera, Toxoptera citricida, Trialeurodes abutilonea, Trialeurodes vaporariorum, Viteus vitifolii;

from the order of the termites (Isoptera), for example, Calotermes flavicollis, Leucotermes flavipes, Macrotermes subhyalinus, Odontotermes formosanus, Reticulitermes lucifugus, ermes natalensis;

from the order of the orthopterous insects (Orthoptera), for example, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca peregrina, Stauronotus maroccanus, Schistocerca gregaria, also Acheta domestica, Blatta orientalis, Blattella germanica, Periplaneta americana;

from the order of the Arachnoidea, for example, phytophagous mites such as Aculops lycopersicae, Aculops pelekassi, Aculus schlechtendali, Brevipalpus phoenicis, Bryobia praetiosa, Eotetranychus carpini, Eutetranychus banksii, Eriophyes sheldoni, Oligonychus pratensis, Panonychus ulmi, Panonychus citri, Phyllocoptruta oleivora, Polyphagotarsonemus latus, Tarsonemus pallidus, Tetranychus cinnabarinus, Tetranychus kanzawai, Tetranychus pacificus, Tetranychus urticae, ticks such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Rhipicephalus appendiculatus* and *Rhipicephalus evertsi* and animal-parasitic mites such as *Dermanyssus gallinae, Psoroptes ovis* and *Sarcoptes scabiei;* from the class of the nematodes, for example, root gall nematodes, eg. *Meloidogyne hapla, Meloidogyne incognita, Meloidogyne javanica*, cyst-forming nematodes, eg. *Globodera pallida, Globodera rostochiensis, Heterodera avenae, Heterodera glycines, Heterodera schachtii*, migratory endoparasites and semi-endoparasitic nematodes, eg. *Heliocotylenchus multicinctus, Hirschmanniella oryzae*, Hoplolaimus spp., *Pratylenchus brachyurus, Pratylenchus fallax, Pratylenchus penetrans, Pratylenchus vulnus, Radopholus similis, Rotylenchus reniformis, Scutellonema bradys, Tylenchulus semipenetrans*, stem and leaf nematodes, eg. *Anguina tritici, Aphelenchoides besseyi, Ditylenchus angustus, Ditylenchus dipsaci*, virus vectors, eg. Longidorus spp., *Trichodorus christei, Trichodorus viruliferus, Xiphinema index, Xiphinema mediterraneum.*

The compounds I can be used as such, in the form of their formulations or the use forms prepared therefrom by spraying, atomizing, dusting, broadcasting or watering, eg. in the form of directly sprayable solutions, powders, suspensions or dispersions, emulsions, oil dispersions, pastes, dusting compositions, broadcasting compositions or granules. The use forms depend entirely on the intended uses; in each case they should if possible guarantee the finest dispersion of the active compounds according to the invention.

The compounds of the formula I are in some cases systemically active as fungicides. They can be employed as folia and soil fungicides against a broad spectrum of phytopathogenic fungi, in particular from the Ascomycetes, Deuteromycetes, Phycomycetes and Basidiomycetes classes.

They are of particular importance for the control of a multiplicity of fungi on various crop plants such as wheat, rye, barley, oats, rice, corn, grass, cotton, soybeans, coffee, sugar cane, grapes, fruit and decorative plants and vegetable plants such as cucumbers, beans and cucurbits, and on the seeds of these plants.

The compounds I are specifically suitable for the control of the following plant diseases:

*Erysiphe graminis* (powdery mildew) in cereals,

*Erysiphe cichoracearum* and *Sphaerotheca fuliginea* on cucurbits,

*Podosphaera leucotricha* on apples,

*Uncinula necator* on vines,

Puccinia species on cereals,

Rhizoctonia species on cotton and grass,

Ustilago species on cereals and sugar cane,

*Venturia inaequalis* (scab) on apples,

Helminthosporium species on cereals,

*Septoria nodorum* on wheat,

*Botrytis cinerea* (gray mold) on strawberries, vines,

*Cercospora arachidicola* on groundnuts,

*Pseudocercosporella herpotrichoides* on wheat, barley,

*Pyricularia oryzae* on rice,

*Phytophthora infestans* on potatoes and tomatoes,

Fusarium and Verticillium species on various plants,

*Plasmopara viticola* on vines,

Alternaria species on vegetables and fruit.

The novel compounds can also be employed in the protection of materials, eg. for the protection of wood, paper and textiles, eg. against *Paecilomyces variotii.*

They can be converted into the customary formulations, such as solutions, emulsions, suspensions, dusts, powders, pastes or granules. The use forms here depend on the particular intended use; in each case they should if possible guarantee the finest dispersion of the active compounds.

The formulations are prepared in a known manner, eg. by extending the active compound with solvents and/or carriers, if desired using emulsifiers and dispersants, where if water is used as a diluent other organic solvents can also be used as auxiliary solvents.

Suitable auxiliaries for this purpose are mainly:

solvents such as aromatics (eg. xylene), chlorinated aromatics (eg. chlorobenzenes), paraffins (eg. petroleum fractions), alcohols (eg. methanol, butanol), ketones (eg. cyclohexanone), amines (eg. ethanolamine, dimethylformamide) and water;

carriers such as ground natural minerals (eg. kaolins, aluminas, talc, chalk) and ground synthetic minerals (eg. highly disperse silica, silicates), emulsifiers such as nonionic and anionic emulsifiers (eg. polyoxyethylene fatty alcohol ethers, alkylsulfonates and arylsulfonates) and dispersants such as lignin-sulfite waste liquors and methylcellulose.

Suitable surface-active substances are the alkali metal, alkaline earth metal and ammonium salts of aromatic sulfonic acids, eg. lignosulfonic, phenolsulfonic, naphthalenesulfonic and dibutylnaphthalenesulfonic acid, and also of fatty acids, alkyl- and alkylarylsulfonates, alkyl-, lauryl ether and fatty alcohol sulfates, as well as salts of sulfated hexa-, hepta- and octadecanols, and also of fatty alcohol glycol ethers, condensation products of sulfonated naphthalene and its derivatives with formaldehyde, condensation products of naphthalene or of the naphthalenesulfonic acids with phenol and formaldehyde, polyoxyethylene octylphenol ether, ethoxylated isooctyl-, octyl- or nonylphenol, alkylphenol or tributylphenylpolyglycol ethers, alkylaryl polyether alcohols, isotridecyl alcohol, fatty alcohol ethylene oxide condensates, ethoxylated castor oil, polyoxyethylene or polyoxypropylenealkyl ethers, lauryl alcohol polyglycol ether acetate, sorbitol esters, lignin-sulfite waste liquors or methylcellulose.

Aqueous use forms can be prepared from emulsion concentrates, dispersions, pastes, wettable powders or water-dispersible granules by addition of water. To prepare emulsions, pastes or oil dispersions, the substrates can be homogenized in water as such or dissolved in an oil or solvent, by means of wetting agents, adhesives, dispersants or emulsifiers. However, concentrates consisting of active substance, wetting agent, adhesive, dispersant or emulsifier and possibly solvent or oil can also be prepared which are suitable for dilution with water.

Powder, scattering and dusting compositions can be prepared by mixing or joint grinding of the active substances with a solid carrier.

Granules, eg. coated, impregnated and homogeneous granules, can be prepared by binding the active compounds to solid carriers.

Solid carriers are mineral earths such as silica gel, silicic acids, silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas and vegetable products, such as cereal flour, tree bark meal, wood meal and nutshell meal, cellulose powder or other solid carriers. The active compound concentrations in the ready-to-use preparations can be varied within relatively wide ranges.

Very generally, the compositions contain from 0.0001 to 95% by weight of active compound.

Formulations containing more than 95% by weight of active compound can be applied highly successfully in the ultra-low volume process (ULV), it even being possible to use the active compound without additives.

For use as fungicides, concentrations of from 0.01 to 95% by weight, preferably of from 0.5 to 90% by weight, of active compound are recommended. For use as insecticides, formulations containing from 0.0001 to 10% by weight, preferably from 0.01 to 1% by weight, are suitable.

The active compounds are normally employed in a purity of from 90% to 100%, preferably from 95% to 100% (according to NMR spectrum).

Examples of such preparations are:

I. a solution of 90 parts by weight of a compound I according to the invention and 10 parts by weight of N-methyl-α-pyrrolidone, which is suitable for application in the form of very small drops;

II. a solution of 20 parts by weight of a compound I according to the invention in a mixture of 80 parts by weight of alkylated benzene, 10 parts by weight of the addition product of from 8 to 10 mol of ethylene oxide to 1 mol of oleic acid N-monoethanolamide, 5 parts by weight of calcium salt of dodecylbenzenesulfonic acid, 5 parts by weight of the addition product of 40 mol of ethylene oxide to 1 mol of castor oil; a dispersion is obtained by finely dispersing the formulation in water.

II. a solution of 20 parts by weight of a compound I according to the invention in a mixture of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil; a dispersion is obtained by finely dispersing the formulation in water.

IV. an aqueous dispersion of 20 parts by weight of a compound I according to the invention in a mixture of 25 parts by weight of cyclohexanone, 65 parts by weight of a petroleum fraction of boiling point from 210 to 280° C. and 10 parts by weight of the addition product of 40 mol of ethylene oxide to 1 mol of castor oil; a dispersion is obtained by finely dispersing the formulation in water.

V. a mixture, ground in a hammer mill, of 20 parts by weight of a compound I according to the invention, 3 parts by weight of the sodium salt of diisobutylnaphthalene-α-sulfonic acid, 17 parts by weight of the sodium salt of a lignosulfonic acid from a sulfite waste liquor and 60 parts by weight of powdered silica gel; a spray mixture is obtained by finely dispersing the mixture in water;

VI. an intimate mixture of 3 parts by weight of a compound I according to the invention and 97 parts by weight of finely divided kaolin; this dusting composition contains 3% by weight of active compound;

VII. an intimate mixture of 30 parts by weight of a compound I according to the invention, 92 parts by weight of powdered silica gel and 8 parts by weight of liquid paraffin which has been sprayed onto the surface of this silica gel; this preparation gives the active compound a good adhesion;

VIII. a stable aqueous dispersion of 40 parts by weight of a compound I according to the invention, 10 parts by weight of the sodium salt of a phenolsulfonic acid/urea/formaldehyde condensate, 2 parts by weight of silica gel and 48 parts by weight of water, which can be further diluted;

IX. a stable oily dispersion of 20 parts by weight of a compound I according to the invention, 2 parts by weight of the calcium salt of dodecylbenzenesulfonic acid, 8 parts by weight of fatty alcohol polyglycol ether, 2 parts by weight of the sodium salt of a phenolsulfonic acid/urea/formaldehyde condensate and 68 parts by weight of a paraffinic mineral oil;

X. a mixture, ground in a hammer mill, of 10 parts by weight of a compound I according to the invention, 4 parts by weight of the sodium salt of diisobutylnaphthalene-α-sulfonic acid, 20 parts by weight of the sodium salt of a lignosulfonic acid from a sulfite waste liquor, 38 parts by weight of silica gel and 38 parts by weight of kaolin. By finely dispersing the mixture in 10,000 parts by weight of water, a spray mixture is obtained which contains 0.1% by weight of the active compound.

The compounds I are applied by treating the fungi or the seeds, plants, materials or the soil to be protected from fungal attack with a fungicidally active amount of the active compounds.

They are applied before or after the infection of the materials, plants or seeds by the fungi.

Depending on the type of effect desired, the application rates are from 0.02 to 3 kg of active compound per ha, preferably from 0.1 to 1 kg/ha.

In seed treatment, amounts of active compound of from 0.001 to 50 g, preferably from 0.01 to 10 g, per kilogram of seed are in general needed.

The application rate of active compound for controlling pests under outdoor conditions is from 0.02 to 10, preferably from 0.1 to 2.0 kg/ha.

The compounds I, on their own or in combination with herbicides or fungicides, can also be applied jointly mixed with further crop protection agents, for example with growth regulators or with agents for controlling pests or bacteria. Of interest is also the miscibility with fertilizers or with mineral salt solutions which are employed for eliminating nutritional and trace element deficiencies.

The crop protection agents and fertilizers can be added to the compositions according to the invention in a weight ratio of from 1:10 to 10:1, if appropriate even immediately before use (tank mix). On mixing with fungicides or insecticides, in many cases an increase in the fungicidal spectrum of action is obtained here.

The following list of fungicides with which the compounds according to the invention can be applied together is intended to illustrate the combination possibilities, but not restrict them:

sulfur, dithiocarbamates and their derivatives, such as ferric dimethyldithiocarbamate, zinc dimethyldithiocarbamate, zinc ethylenebisdithiocarbamate, manganese ethylenebisdithiocarbamate, manganese zinc ethylenediamine bisdithiocarbamate, tetramethylthiuram disulfide, ammonia complex of zinc N,N-ethylenebisdithiocarbamate, ammonia complex of zinc N,N'-propylenebisdithiocarbamate, zinc N,N'-propylenebisdithiocarbamate, N,N'-polypropylenebis (thiocarbamoyl) disulfide; nitro derivatives, such as dinitro(1-methylheptyl)phenyl crotonate, 2-sec-butyl-4,6-dinitrophenyl 3,3-dimethylacrylate, 2-sec-butyl-4,6-dinitrophenyl isopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-β-[bis-(dimethylamino)-phosphinyl]-3-phenyl-1,2,4-triazole, 2,3-dicyano-1,4-dithioanthraquinone, 2-thio-1,3-dithiolo-β-[4,5-b]quinoxaline, methyl 1-(butylcarbamoyl)-2-benzimidazolecarbamate, 2-methoxycarbonylaminobenzimidazole, 2-(fur-2-yl)benzimidazole, 2-(thiazol-4-yl)benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)3-methyl-5-isoxazolone, 2-thiopyridine-1-oxide, 8-hydroxyquinoline or its copper salt, 2,3-dihydro-5-carboxanilido-6-methyl-1,4-oxathiin, 2,3-dihydro-5-carboxanilido-6-methyl-1,4-oxathiin-4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis(1-(2,2,2-trichloroethyl))formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tertbutylphenyl)-2methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, and also various fungicides, such as dodecylguanidine acetate, 3-[3-(3,5-dimethyl-2-oxycyclohexyl)-2-hydroxyethyl]glutarimide, hexachlorobenzene, DL-methyl-N-(2,6-dimethylphenyl)-N-2-furoyl alaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-ethylaminocarbonyl-2-methoximino]acetamide, 1-[2-(2,4-dichlorophenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl)methyl)-1-H-1,2,4-pyrazole.

SYNTHESIS EXAMPLES

The procedures presented in the Synthesis Examples below were used with appropriate modification of the starting compounds to obtain further compounds I. The compounds thus obtained are listed with physical data in the following Table.

1. Methyl N-(2-(N'-(p-methylphenyl)-4'-chloropyrazolyl-3'-oxy-methyl)phenyl)-N-methoxycarbamate (Table, No. 19)

A mixture of 1.7 g (purity about 75%, ≙4.6 mmol) of methyl N-(2-bromomethylphenyl)-N-methoxycarbamate (WO 93/15046), 1 g (4.8 mmol) of N-(p-methylphenyl)-4-chloro-3-hydroxypyrazole and 1 g (7.2 mmol) of $K_2CO_3$ in 15 ml of DMF is stirred at room temperature overnight. The reaction mixture is then diluted with water and the aqueous phase is extracted three times with methyl t-butyl ether. The combined organic phases are extracted with water, dried over $MgSO_4$ and concentrated. The residue is then chromatographed on $Al_2O_3$ using methylene chloride and subsequently on silica gel using cyclohexane/ethyl acetate mixtures. 1.4 g (68%) of the title compound are obtained as a pale yellow oil.

$^1$H-NMR($CDCl_3$; δ in ppm): 7.75 (s, 1H, pyrazolyl); 7.70 (m, 1H, phenyl); 7.5 (m, 5H, phenyl); 7.2 (d, 2H, phenyl); 5.4 (s, 2H, $OCH_2$); 3.75, 3.8 (2s, each 3H, 2×$OCH_3$); 2.35 (s, 3H, $CH_3$)

2. N-Methyl-N'-methoxy-N'-(2-((N''-pyrazinyl)pyrazolyl-3''-oxymethyl)phenyl)urea (Table, No. 32)

a) Phenyl N-hydroxy-N-(2-methylphenyl)carbamate

A mixture of 350 g (purity about 80%; 2.3 mol; prepared by a similar method to Bamberger et al., Ann. Chem. 316 (1901), 278) of N-(2-methylphenyl)hydroxylamine and 286.8 g (3.4 mol) of $NaHCO_3$ in 700 ml of $CH_2Cl_2$ is treated with 447 g (2.85 mol) of phenyl chloroformate with vigorous stirring at about −10° C. The mixture is stirred for about 1 hour at −10° C. and 600 ml of water are then added dropwise, the temperature of the reaction mixture increasing to 5–10° C. and a vigorous evolution of gas occurring. The aqueous phase is then separated off and extracted once more with $CH_2Cl_2$. The combined organic phases are extracted with water, dried over $MgSO_4$ and concentrated. The residue crystallizes and is stirred with cyclohexane. 407 g (72%) of the title compound are obtained as a colorless solid.

$^1$H-NMR($CDCl_3$; δ in ppm): 8.6 (s, broad, 1H, OH); 7.0–7.4 (m, 9H, phenyl), 2.4(s,3H,$CH_3$)

b) Phenyl N-methoxy-N-(2-methylphenyl)carbamate

A mixture of 407 g (1.6 mol) of N-hydroxy-N-(2-methylphenyl)carbamate (Example 2a) and 277 g (2.0 mol) of $K_2CO_3$ in 700 ml of $CH_2Cl_2$ is treated dropwise with 211 g (1.67 mol) of dimethyl sulfate. The reaction mixture warms to about 40° C. during the course of this. The reaction mixture is stirred overnight at room temperature and then filtered through kieselguhr. The filtrate is washed with $NH_3$ soln. and water, dried over $MgSO_4$ and concentrated. The residue crystallizes and is stirred with hexane. 324 g (75%) of the title compound are obtained as colorless solid.

$^1$H-NMR($CDCl_3$; δ in ppm): 7.1–7.6 (m, 9H, phenyl); 3.8 (s,3H,$OCH_3$); 2.4 (s, 3H, $CH_3$)

c) Phenyl N-Methoxy-N-(2-bromomethylphenyl)carbamate

A mixture of 324 g (1.3 mol) of phenyl N-methoxy-N-(2-methylphenyl)carbamate (Example 2b), 258 g (1.45 mol) of N-bromosuccinimide and 1 g of azoisobutyronitrile in 1 l of CCl₄ is irradiated using a 300 W UV lamp for about 6 hours, whereby the reaction mixture is heated to boiling. 13 g of N-bromosuccinimide are then added and the mixture is irradiated for a further 8 hours. It is then cooled to room temperature and the precipitated succinimide is filtered off. The organic phase is then extracted with water, dried over MgSO₄ and concentrated. The residue crystallizes and is stirred with cyclohexane. 300 g (68%) of the title compound are obtained as a beige solid.

¹H-NMR(CDCl₃; δ in ppm): 7.0–7.6 (m, 9H, phenyl) ;4.65 (s,2H,CH₂-Br); 3.9 (s, 3H, OCH₃)

d) Phenyl N-Methoxy-N-(2-((N'-pyrazinyl)pyrazolyl-3'-oxymethyl)phenyl)carbamate

A mixture of 3.1 g (9.2 mmol) of phenyl N-methoxy-N-(2-bromomethylphenyl)carbamate (Example 2c), 1.5 g (9.2 mmol) of N-pyrazinyl-3-hydroxypyrazole and 2 g (14.5 mmol) of K₂CO₃ in 10 ml of DMF is stirred at room temperature overnight. The reaction mixture is then diluted with water and extracted three times with methyl t-butyl ether. The combined organic phases are extracted with water, dried over MgSO₄ and concentrated. The residue is purified by column chromatography using cyclohexane/ethyl acetate mixtures. 2.4 g (63%) of the title compound are obtained as a yellow oil.

¹H-NMR(CDCl₃; δ in ppm): 9.15 (d, 1H, pyrazolyl); 8.3 (m, 3H, pyrazinyl); 7.7 (m, 1H, phenyl); 7.1–7.6 (m, 8H, phenyl); 6.0 (d, 1H, pyrazolyl); 5.5 (s, 2H, OCH₂); 3.85 (s, 3H, OCH₃)

e) N-Methyl-N'-methoxy-N'-(2-((N'-pyrazinyl)pyrazolyl-3'-oxymethyl)phenyl)urea

A mixture of 1.9 g (4.6 mmol) of phenyl N-ethoxy-N-(2-((N'-pyrazinyl)pyrazolyl-3'-oxymethyl)phenyl)carbamate (Example 2d) and 15 ml of aqueous methylamine solution (40% strength) is stirred overnight at room temperature. Water is then added and the aqueous phase is extracted twice with methylene chloride. The combined organic phases are washed with water, dried over MgSO₄ and concentrated. The residue crystallizes and is stirred with cyclohexane. 0.9 g (55%) of the title compound are obtained as a beige solid.

¹H-NMR(CDCl₃; δ in ppm): 9.15 (d, 1H, pyrazolyl); 8.3 (m, 3H, pyrazinyl); 7.6 (m, 1H, phenyl); 7.35 (m, 3H, phenyl); 6.0 (m, 2H, NH, pyrazinyl); 5.45 (s, 2H, OCH₂); 3.7 (s, 3H, OCH₃); 2.9 (d, 3H, NCH₃)

TABLE

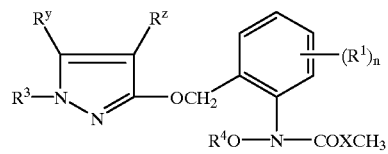

I.A

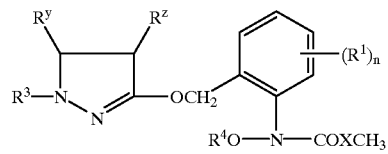

I.B

| No. | Structure | $R_n^1$ | $R^y$ | $R^z$ | $R^3$ | $R^4$ | X | M.p. [° C.], IR [cm⁻¹] |
|---|---|---|---|---|---|---|---|---|
| 1 | I.A | H | H | H | C₆H₅ | CH₃ | O | 1737, 1600, 1493, 1480, 1456, 1358, 1332, 755 |
| 2 | I.A | H | H | H | 4-Cl—C₆H₄ | CH₃ | O | 1737, 1547, 1503, 1480, 1457, 1441, 1350, 1094, 1030, 936 |
| 3 | I.A | H | H | H | 2,4-Cl₂—C₆H₃ | CH₃ | O | 1739, 1547, 1492, 1475, 1457, 1440, 1356, 1107, 1058, 1027 |
| 4 | I.A | H | H | H | 2-CH₃—C₆H₄ | CH₃ | O | 1739, 1710, 1542, 1482, 1457, 1440, 1358, 1052, 1030, 763 |
| 5 | I.A | H | H | H | 3-CH₃—C₆H₄ | CH₃ | O | 1738, 1593, 1545, 1494, 1483, 1457, 1441, 1357, 1056, 1032 |
| 6 | I.A | H | H | H | 4-CH₃—C₆H₄ | CH₃ | O | 1738, 1544, 1519, 1482, 1456, 1440, 1393, 1358, 1243, 1031, |
| 7 | I.A | H | H | H | 2-Cl—C₆H₄ | CH₃ | O | 1739, 1710, 1546, 1495, 1476, 1453, 1441, 1358, 1027, 757 |
| 8 | I.A | H | H | H | 3-Cl—C₆H₄ | CH₃ | O | 1736, 1597, 1548, 1495, 1476, 1456, 1440, 1357, 1101, 771 |
| 9 | I.A | H | H | H | 2,6-Cl₂—C₆H₃ | CH₃ | O | 1727, 1543, 1464, 1445, 1364, 1348, 791, 785, 749, |
| 10 | I.A | H | H | H | 3,5-Cl₂—C₆H₄ | CH₃ | O | 120 |
| 11 | I.A | H | H | H | 2,5-Cl₂—C₆H₃ |  | O | 1737, 1710, 1547, 1489, 1471, 1456, 1437, 1346, 1096, 1027 |
| 12 | I.A | H | H | H | 3,4-Cl₂—C₆H₃ | CH₃ | O | 85 |
| 13 | I.A | H | H | H | 2-CH₃, 4-Cl—C₆H₃ | CH₃ | O | 1738, 1710, 1543, 1494, 1480, 1457, 1441, 1358, 1100, 940 |
| 14 | I.A | H | H | H | 3-CF₃—C₆H₄ | CH₃ | O | 1721, 1558, 1459, 1441, 1368, 1333, 1121, 1067, 793, 764 |
| 15 | I.A | H | H | H | 4-OCH₃—C₆H₄ | CH₃ | O | 1737, 1541, 1517, 1483, 1457, |

TABLE-continued

I.A: Structure with pyrazole ring bearing R³-N, R^y, R^z substituents, connected via OCH₂ to a phenyl ring with (R¹)ₙ and R⁴O—N—COXCH₃ group.

I.B: Similar to I.A but with a dihydropyrazole (pyrazoline) ring.

| No. | Structure | R¹ₙ | R^y | R^z | R³ | R⁴ | X | M.p. [° C.], IR [cm⁻¹] |
|---|---|---|---|---|---|---|---|---|
| 16 | I.A | H | CH₃ | H | C₆H₅ | CH₃ | O | 1442, 1359, 1250, 1056, 1032 1739, 1710, 1560, 1504, 1484, 1456, 1440, 1380, 1359, 760 |
| 17 | I.A | H | H | CH₃O—CO | C₆H₅ | CH₃ | O | 1720, 1702, 1570, 1540, 1446, 1372, 1357, 1285, 1119, 751 |
| 18 | I.A | H | H | H | 4-F—C₆H₄ | CH₃ | O | 1737, 1546, 1516, 1482, 1457, 1440, 1359, 1233, 1031, 835 |
| 19 | I.A | H | H | Cl | 4-CH₃—C₆H₄ | CH₃ | O | 1738, 1554, 1509, 1456, 1440, 1358, 1253, 1118, 940, 760 |
| 20 | I.A | H | 3-F | H | 2,4-Cl₂—C₆H₃ | CH₃ | O | 90 |
| 21 | I.A | H | 3-F | H | 2,4-Cl₂—C₆H₃ | CH₃ | O | 109 |
| 22 | I.A | H | H | H | 3-OCH₃—C₆H₄ | CH₃ | O | 1737, 1607, 1597, 1545, 1499, 1482, 1472, 1440, 1358 |
| 23 | I.A | H | H | Cl | 2,4-Cl₂—C₆H₃ | CH₃ | O | 110 |
| 24 | I.A | H | CF₃ | H | 2,4-Cl₂—C₆H₄ | CH₃ | O | 1739, 1507, 1486, 1457, 1359, 1250, 1190, 1139, 1109, 1092 |
| 25 | I.A | H | CH₃ | H | 2,4-Cl₂—C₆H₃ | CH₃ | O | 1738, 1710, 1567, 1561, 1500, 1484, 1456, 1440, 1359, 1104 |
| 26 | I.A | H | H | Cl | 4-Cl—C₆H₄ | CH₃ | O | 1729, 1553, 1511, 1497, 1438, 1356, 1332, 1265, 1122, 1112 |
| 27 | I.A | H | H | H | 3,4-(OCF₂O)—C₆H₃ | CH₃ | O | 97 |
| 28 | I.A | H | H | H | 2-pyridyl | CH₃ | O | 85 |
| 29 | I.A | H | H | H | 5-CF₃-pyridyl-2 | CH₃ | O | 81 |
| 30 | I.A | H | H | H | 2-pyrazinyl | CH₃ | O | 87 |
| 31 | I.B | H | H | H | C₆H₆ | CH₃ | O | 1739, 1639, 1599, 1501, 1456, 1439, 1411, 1354, 1252, 752 |
| 32 | I.A | H | H | H | 2-pyrazinyl | CH₃ | NH | 145 |
| 33 | I.A | H | H | NO₂ | 5-CF₃-pyri-dyl-2 | CH₃ | O | 126 |
| 34 | I.A | H | CH₃ | H | 4-Cl—C₆H₄ | CH₃ | O | 1738, 1561, 1500, 1456, 1440, 1359, 1094, 1010, 764 |
| 35 | I.A | H | H | H | 6-Cl-Pyridazin-3-yl | CH₃ | O | 135 |
| 36 | I.A | H | H | H | 5-Cl-Pyridin-2-yl | CH₃ | O | 77 |
| 37 | I.A | H | H | CF₃ | Cyclohexyl | CH₃ | O | 1743, 1496, 1456, 1441, 1359, 1272, 1262, 1176, 1124, 1029 |
| 38 | I.A | H | H | Cl | 5-Cl-Pyridin-2-yl | CH₃ | O | 92 |
| 39 | I.A | H | H₃CO₂C | H | CH₂C₆H₅ | CH₃ | O | 71 |
| 40 | I.A | H | H | H | C₆H₅ | H | O | 1718, 1600, 1545, 1507, 1481, 1458, 1399, 1359, 1032, 757 |
| 41 | I.A | H | H | H | C₆H₅ | CH₃ | NH | 1675, 1600, 1545, 1508, 1479, 1462, 1399, 1355, 1054, 756 |
| 42 | I.A | H | H | H | C₆H₅ | CH₃ | — | 1680, 1600, 1545, 1507, 1480, 1456, 1359, 1056, 1032, 758 |
| 43 | I.A | H | H | H | C₆H₅ | H | NH | 1653, 1601, 1545, 1707, 1479, 1454, 1414, 1398, 1355, 755 |
| 44 | I.A | H | H | H | C₆H₅ | CH₃ | CH₂ | 1678, 1600, 1545, 1480, 1456, 1394, 1378, 1358, 1055, 756 |
| 45 | I.A | H | H | H | C₆H₅ | H | — | 1643, 1622, 1601, 1544, 1493, 1480, 1368, 1027, 759, 745 |
| 46 | I.A | H | H | H | C₆H₅ | H | CH₂ | 1619, 1600, 1550, 1495, 1482, 1462, 1454, 1358, 765, 753 |
| 47 | I.A | H | H | H | 2,4-Cl₂-Phenyl | CH₃ | NH | 130 |
| 48 | I.A | H | H | H | 4-Cl—C₆H₄ | H | O | 105 |
| 49 | I.A | H | H | H | 4-Cl—C₆H₄ | H | NH | 1653, 1546, 1503, 1480, 1455, 1426, 1390, 1357, 1094, 1071 |
| 50 | I.A | H | H | H | 4-Cl—C₆H₄ | CH₃ | NH | 1675, 1546, 1503, 1479, 1457, 1425, 1389, 1355, 936, 829 |

TABLE-continued

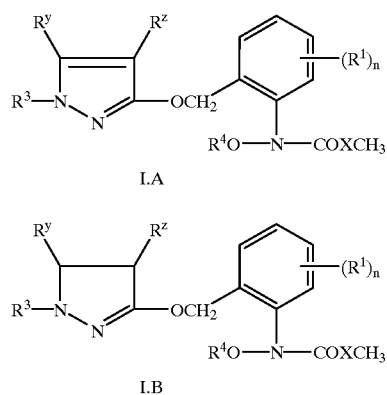

| No. | Structure | $R_n^1$ | $R^y$ | $R^z$ | $R^3$ | $R^4$ | X | M.p. [° C.], IR [cm$^{-1}$] |
|---|---|---|---|---|---|---|---|---|
| 51 | I.A | H | H | H | $CH_2C_6H_5$ | $CH_3$ | O | 1737, 1709, 1537, 1488, 1456, 1439, 1359, 1325, 1032, 733 |
| 52 | I.A | H | H | H | $CH_2$-[4-Cl—$C_6H_4$] | $CH_3$ | O | 1735, 1709, 1538, 1492, 1456, 1439, 1358, 1323, 1096, 761 |
| 53 | I.A | H | H | H | 2,4-$(CH_3)_2$—$C_6H_3$ | $CH_3$ | O | 92 |
| 54 | I.A | H | H | Cl | 2-Pyrazinyl | $CH_3$ | O | 114 |
| 55 | I.B | H | H | H | 4-Cl—$C_6H_4$ | $CH_3$ | O | 1740, 1639, 1599, 1495, 1456, 1439, 1415, 1355, 1251, 1092 |
| 56 | I.A | H | H | H | 2-Cl, 4-F—$C_6H_3$ | $CH_3$ | O | 1737, 1547, 1505, 1494, 1480, 1457, 1441, 1358, 1258, 1028 |

Examples of the Action Against Harmful Fungi

It was possible to show the fungicidal action of the compounds of the formula I by the following tests:

The active compounds were prepared as a 20% strength emulsion in a mixture of 70% by weight of cyclohexanone, 20% by weight of Nekanil® LN (Lutensol® AP6, wetting agent having emulsifier and dispersant action based on ethoxylated alkylphenols) and 10% by weight Emulphor® EL (Emulan® EL, emulsifier based on ethoxylated fatty alcohols) and diluted with water according to the concentration desired.

Activity Against *Puccinia recondita*

Leaves of wheat seedlings (Kanzler variety) were dusted with spores of brown rust (*Puccinia recondita*). The plants treated in this way were incubated for 24 h at 20–22° C. and a relative atmospheric humidity of 90–95% and then treated with the aqueous active compound preparation (63 ppm of active compound). After a further 8 days at 20–22° C. and 65–70% relative atmospheric humidity, the extent of fungal development was determined. Assessment was carried out visually.

In this test, the plants treated with the compounds 2–6, 8, 11–15, 18–20, 22, 23 and 26–29 according to the invention showed 5% or less attack, while the plants treated with a compound (Table 7, Example No. 8) disclosed in WO-A 93/15,046 were attacked to 25%. The untreated plants were attacked to 70%.

In a corresponding experiment, the plants treated with 250 ppm of compound No. 1 according to the invention showed an attack of 3% while plants which were treated with 250 ppm of a compound (Table 7, No. 21) disclosed in WO-A 93/15,046 were attacked to 70%, like the untreated plants.

In a corresponding experiment, the plants treated with 250 ppm of compound Nos. 1–8, 10–16, 18–20, 22, 23, 27–30, 34, 36–38, 41, 47 and 51–56 according to the invention showed an attack of 15% and less while plants which were treated with 250 ppm of a compound (Table 7, No. 21) disclosed in WO-A 93/15,046 were attacked to 70%, like the untreated plants.

Activity Against *Plasmopara viticola*

Potted vines (variety: Muller Thurgau) were sprayed with the active compound preparation until dripping wet. After 8 days, the plants were sprayed with a zoospore suspension of the fungus *Plasmopara viticola* and kept at high atmospheric humidity for 5 days at 20–30° C. Before assessment, the plants were then kept at high atmospheric humidity for 16 h. Assessment was carried out visually.

In this test, the plants treated with the compounds 1–3, 5, 6, 13, 15 and 29 according to the invention showed an attack of 10% or less, while the plants treated with a compound (Table 7, Example No. 8) disclosed in WO-A 39/15,046 were attacked to 25%. The untreated plants were attacked to 70%.

Activity Against *Botrytis cinerea* (Gray Mould)

Paprika seedlings (variety: Neusiedler Ideal Elite) having 4–5 leaves were sprayed until dripping wet with the active compound preparation (application rate: 500 ppm). After drying off, the plants were sprayed with a conidia suspension of the fungus *Botrytis cinerea* and kept for 5 days at 22–24° C. at high atmospheric humidity. Assessment was carried out visually.

In this test, the plants treated with compound No. 1 according to the invention showed no attack, while the plants treated with a compound (Table 7, No. 21) disclosed in WO-A 93/15,046 were attacked to 70%. The untreated plants were attacked to 80%.

Activity Against *Erysiphe graminis var. tritici*

Leaves of wheat seedlings (Frühgold variety) were first treated with the aqueous preparation (application rate 250 ppm) of the active compounds. After about 24 h, the plants were dusted with spores of wheat mildew (*Erysiphe graminis var. tritici*). The plants treated in this way were then incubated for 7 days at 20–22° C. and a relative atmospheric humidity of 75–80%. The extent 0f fungal development was then determined.

In this test, the plants treated with compound No. 1 according to the invention showed no attack, while the plants treated with a compound (Table 7, No. 21) disclosed in WO-A 93/15,046 were attacked to 25%. The untreated plants were attacked to 70%.

In a corresponding experiment, the plants treated with 250 ppm of compound Nos. 1–7, 10, 13, 14, 18–20, 27–29, 34, 36, 41, 50 and 56 according to the invention showed an attack of 15% or less, while plants which were treated with 250 ppm of a compound (Table 7, No. 21) disclosed in WO-A 93/15,046 were attacked to 25%. The untreated plants were attacked to 70%.

In a corresponding experiment, the plants treated with 63 ppm of compound Nos. 1–7, 10, 13, 14, 18–20, 27–29, 34, 36, 41, 50 and 56 according to the invention showed an attack of 15% or less, while plants which were treated with 250 ppm of a compound (Table 7, No. 21) disclosed in WO-A 93/15,046 were attacked to 40%. The untreated plants were attacked to 70%.

In a corresponding experiment, the plants treated with 16 ppm of compound Nos. 1–7, 10, 13, 14, 18–20, 27–29, 34, 36, 41, 50 and 56 according to the invention showed an attack of 25% or less, while plants which were treated with 250 ppm of a compound (Table 7, No. 21) disclosed in WO-A 93/15,046 were attacked to 65%. The untreated plants were attacked to 70%.

Examples of the action against animal pests

It was possible to show the action of the compounds of the general formula I against animal pests by the following tests: The active compounds were prepared and diluted with acetone in the case of a) or with water in the case of b) according to the desired concentration.

After conclusion of the tests, the lowest concentration at which the compounds still caused an 80–100% inhibition or mortality in comparison with untreated control tests was determined in each case (activity threshold or minimum concentration).

We claim:

1. An intermediate of the formula XII

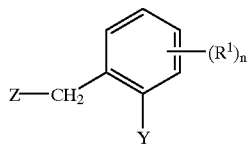

where the substituents and the index have the following meanings:

n is 0, 1, 2, 3 or 4, it being possible for the substituents $R^1$ to be different if n is greater than 1;

$R^1$ is nitro, cyano, halogen, unsubstituted or substituted alkyl, alkenyl, alkynyl, alkoxy, alkenyloxy, alkynyloxy or in the case where n is 2, additionally is an unsubstituted or substituted bridge bonded to two adjacent ring atoms and containing three to four members from the group consisting of 3 or 4 carbon atoms, 1 to 3 carbon atoms and 1 or 2 nitrogen, oxygen and/or sulfur atoms, this bridge together with the ring to which it is bonded being able to form a partly unsaturated or aromatic radical;

Y is $NO_2$, NHOH or $NHOR^4$, $R^4$ is unsubstituted or substituted alkyl, alkenyl, alkynyl, cycloalkyl, cycloalkenyl, alkylcarbonyl or alkoxycarbonyl;

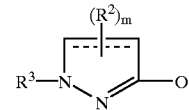

m is 0, 1 or 2, it being possible for the substituents $R^2$ to be different if m is greater than 1;

$R^2$ is nitro, cyano, halogen, $C_1$–$C_4$-alkyl, $C_1$–$C_4$-haloalkyl, $C_1$–$C_4$-alkoxy, $C_1$–$C_4$-alkylthio or $C_1$–$C_4$-alkoxycarbonyl;

$R^3$ is unsubstituted or substituted alkyl, alkenyl or alkynyl;

an unsubstituted or substituted, saturated or mono- or diunsaturated ring which, in addition to carbon atoms, can contain one to three of the following heteroatoms as ring members: oxygen, sulfur and nitrogen, or an unsubstituted or substituted, mono- or binuclear aromatic radical which, in addition to carbon atoms, can contain one to four nitrogen atoms or one or two nitrogen atoms and one oxygen or sulfur atom or one oxygen or sulfur atom as ring members.

2. An intermediate of the general formula XIII

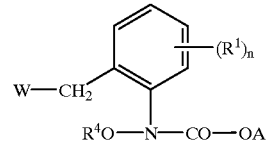

where $R^1$ is nitro, cyano, halogen, unsubstituted or substituted alkyl, alkenyl, alkynyl, alkoxy, alkenyloxy, alkynyloxy or in the case where n is 2, $R^1$ is an unsubstituted or substituted bridge bonded to two adjacent ring atoms and containing three to four members from the group consisting of 3 or 4 carbon atoms, 1 to 3 carbon atoms and 1 or 2 nitrogen, oxygen and/or sulfur atoms, this bridge together with the ring to which it is bonded being able to form a partly unsaturated or aromatic radical;

$R^4$ is hydrogen, unsubstituted or substituted alkyl, alkenyl, alkynyl, cycloalkyl, cycloalkenyl, alkylcarbonyl or alkoxycarbonyl;

and n is 0, 1, 2, 3 or 4, it being possible for the substituents $R^1$ to be different if n is greater than 1;

and

W is a group $Z^a$ which has the meaning given in claim 6, and

A is phenyl.

* * * * *

UNITED STATES PATENT AND TRADEMARK OFFICE
CERTIFICATE OF CORRECTION

Page 1 of 1

PATENT NO.       : 6,054,592
APPLICATION NO.  : 09/131640
DATED            : April 25, 2000
INVENTOR(S)      : Bernd Mueller et al.

It is certified that error appears in the above-identified patent and that said Letters Patent is hereby corrected as shown below:

In col. 44, line 5, insert the following:

--$Z$   is a group $Z^a$--.

In col. 44, line 60, delete "claim 6" and insert --claim 1--.

Signed and Sealed this
Twelfth Day of April, 2011

David J. Kappos
*Director of the United States Patent and Trademark Office*